(12) United States Patent
Chamberlain et al.

(10) Patent No.: US 10,351,618 B2
(45) Date of Patent: *Jul. 16, 2019

(54) UTI FUSION PROTEINS

(71) Applicant: Takeda Pharmaceutical Company Limited, Osaka (JP)

(72) Inventors: Aaron Chamberlain, San Diego, CA (US); Qiang Liu, Palo Alto, CA (US); Mathias Schmidt, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/823,398

(22) Filed: Nov. 27, 2017

(65) Prior Publication Data

US 2018/0072795 A1    Mar. 15, 2018

Related U.S. Application Data

(62) Division of application No. 15/120,956, filed as application No. PCT/US2015/017152 on Feb. 23, 2015, now Pat. No. 9,856,310.

(60) Provisional application No. 61/943,617, filed on Feb. 24, 2014.

(51) Int. Cl.
   *C07K 14/81*     (2006.01)
   *A61K 38/00*    (2006.01)

(52) U.S. Cl.
   CPC .......... *C07K 14/8114* (2013.01); *A61K 38/00* (2013.01); *C07K 2319/30* (2013.01); *C07K 2319/50* (2013.01); *C07K 2319/91* (2013.01)

(58) Field of Classification Search
   None
   See application file for complete search history.

(56) References Cited

U.S. PATENT DOCUMENTS

| 5,407,915 A | 4/1995 | Fritz et al. |
| 5,409,895 A | 4/1995 | Morishita et al. |
| 5,541,288 A | 7/1996 | Nakano et al. |
| 5,792,629 A | 8/1998 | Morishita et al. |
| 6,583,108 B1 | 6/2003 | Tamburini et al. |
| 7,019,123 B2 | 3/2006 | Tamburini et al. |
| 9,856,310 B2 * | 1/2018 | Chamberlain ..... C07K 14/8114 |
| 2008/0181892 A1 | 7/2008 | Ledbetter et al. |
| 2008/0255025 A1 | 10/2008 | Ladner |

FOREIGN PATENT DOCUMENTS

| CN | 103044554 | 4/2013 |
| CN | 103044554 A | 4/2013 |
| JP | 2013-25309 | 12/2013 |
| JP | 2013 253079 | 12/2013 |
| JP | 2013253079 A * | 12/2013 |

OTHER PUBLICATIONS

Pifferi et al., "The Safety of pharmaceutical excipients", Ill Farmaco, 2003, pp. 541-550 (Year: 2003).*
Martinez et al. "Expression systems for recombinant proteins (II). Producing organisms.", Biotech Spain, 2010, pp. 1-6 (Year: 2010).*
Morishita et al., Thrombosis Research 1994, vol. 73 (3/4) p. 193-204.
Fries et al, International Journal of Biochemistry and Cell Biology, 2000, vol. 32, p. 125-137.

* cited by examiner

*Primary Examiner* — Lianko G Garyu
(74) *Attorney, Agent, or Firm* — Diana M. Steel; Matthew J. Russo; David M. Stemerick

(57) ABSTRACT

The present invention provides UTI fusion proteins, DNA sequences for producing the same, and pharmaceutical compositions and methods of using the same.

16 Claims, 10 Drawing Sheets
Specification includes a Sequence Listing.

FIGURE 7

Compound IC50 (M)

| Target | UTI-Fc (UFC1) | Control I IC50 (M) | Control compound |
|---|---|---|---|
| Caspase 1 | 1.33E-06 | 7.30E-08 | IETD-CHO |
| Cathepsin C | 5.48E-06 | 2.29E-07 | E 64 |
| Cathepsin G | > 1.0E-05 | 6.53E-07 | Chymostatin |
| Chymotrypsin | 9.35E-08 | < 5.08E-10 | Chymostatin |
| Papain | 3.29E-06 | < 5.08E-10 | E64 |
| Plasmin | 6.63E-08 | 6.14E-08 | Gabexate Mesylate |
| Proteinase K | | 8.71E-06 | Proteinase K inhibitor |
| TACE/ADAM17 | > 1.0E-05 | 1.69E-08 | GM6001 |
| Thrombin | | 2.60E-06 | Gabexate Mesylate |
| Tryptase beta II | | 1.61E-09 | Gabexate Mesylate |

FIGURE 9

| Protein Name | PFR# | Titer(ug/mL) | Concentration(mg/mL) | volume(mL) | Yield(mgs) | Load volume(mL) | % Recovery |
|---|---|---|---|---|---|---|---|
| UTI-Fc(3Ser) | 711 | 45 | 2.8 | 2 | 5.50 | 208 | 68.7 |
| UTI-Fc(3Ser)-Ser10Ala | 712 | 52 | 3.4 | 2 | 6.75 | 208 | 65.5 |
| UTI-Fc(3Ser)-K21S/K22S | 713 | 40 | 2.3 | 2 | 4.67 | 208 | 58.1 |
| UTI m1-Fc(3Ser) | 714 | 51 | 2.9 | 2 | 5.71 | 208 | 56.5 |
| UTI m2-Fc(3Ser) | 715 | 2 | | | | | |
| UTI d1-Fc(3Ser) | 716 | 41 | 2.5 | 2 | 4.94 | 208 | 60.7 |
| UTI d2-Fc(3Ser) | 717 | 52 | 2.7 | 2 | 5.42 | 208 | 52.3 |
| UTI L1-Fc(3Ser) | 718 | 33 | 2.1 | 2 | 4.18 | 208 | 62.7 |
| UTI L2-Fc(3Ser) | 719 | 40 | 2.4 | 2 | 4.80 | 208 | 60.3 |
| UTI L3-Fc(3Ser) (Gly4Ser)2 linker | 720 | 38 | 2.5 | 2 | 4.93 | 208 | 64.7 |
| UTI-Fc(IgG2) | 721 | 39 | 2.5 | 2 | 5.06 | 208 | 64.3 |
| Fc(3Ser)-UTI (Gly4Ser)3 linker | 722 | 31 | 1.9 | 2 | 3.85 | 208 | 62.8 |
| mouse UTI - mouse IgG1 | 723 | 4 | | | | | |

UTI FUSION PROTEINS

CROSS-REFERENCE TO RELATED APPLICATIONS

This application is a divisional of U.S. application Ser. No. 15/120,956, filed Aug. 23, 2016, which is the U.S. National Stage entry under 35 U.S.C. § 371(c) of International Application PCT/US2015/017152, filed Feb. 23, 2015, which claims the benefit of U.S. Provisional Application No. 61/943,617, filed Feb. 24, 2014.

FIELD OF THE INVENTION

The present invention relates to molecular biology, pharmacology, and medicine.

BACKGROUND OF THE INVENTION

Urinary Trypsin Inhibitor (UTI), also known as ulinastatin, uristatin, urinastatin, ulistin, human inhibitor 30 (HI-30), mingin and bikunin, is a protease inhibitor with a molecular weight of about 40 kD. UTI is present in human urine and blood (hUTI) and has a variety of physiological activities such as an inhibitory effect on a family of serine proteases, such as trypsin, α-chymotrypsin, plasmin, cathepsin-G and leukocyte elastase. UTI also has immunomodulatory effect, and it can down-regulate the release of proinflammatory cytokines, such as tumor necrosis factor-α (TNF-α), interleukin-1 (IL-1) and interleukin (IL-6). In addition, UTI also interferes with PDGF-D (PDGF-DD)/PDGF-BBR active dimer-mediated signaling pathway by neutralizing the dimer.

hUTI has received marketing authorization and one product is marketed in Japan under the trade name Miraclid and is isolated from human urine. In fact, hUTI isolated from human urine is currently marketed by several manufacturers for treatment of pancreatitis and acute circulatory failure caused by shock.

UTI is first produced in humans as a presursor protein called AMBP (α1-microglobulin/bikunin precursor), which is encoded on human chromosome 9. The proteolysis of AMBP yields the free UTI containing 143 amino acids. UTI comprises two Kunitz domains that are known to inhibit serine proteases, which are flanked by unstructured amino acids on UTI's N- and C-termini. The two domains are expected to confer differenct specificities of protease inhibition, due to the different amino acids involved in protease binding. By analogy to other serine protease inhibitors (e.g. BPTI, bovine pancreatic trypsin inhibitor), we can estimate that two key amino acids for protease inhibition include Met26 (Kunitz domain 1) and Arg88 (Kunitz domain 2). Little is know about the involvement of different portions of UTI during inhibition of different proteases, but removal of Kunitz domain 1 has been shown to change proteases specificity, uncovering new inhibitory activity against Factor Xa and plasma kallikrien. The full-length UTI does not show inhibition of these two proteases (Morishita et al., Thrombosis Research 1994, vol 73 (3/4) p 193-204). UTI also comprises two attached sugars, one O-linked at Ser10 and one N-linked at Asn45. The half-life of UTI in rodents and humans is 4-30 minutes (Fries et al, International Journal of Biochemistry and Cell Biology, 2000, vol 32, p 125-137).

A UTI fusion protein should contain optimized sequence of amino acids, including the best start and stop points of any UTI domains, and may be fused to another protein to enhance properties such as expression, purification, half-life, and stability. The exact sequence of the fusion partner needs determination and may include variations in linkers, start/stop points, and/or mutations that may change the functional properties of the fusion partner.

Variants of ulinastatin obtained from urine are known WO199856916, U.S. Pat. Nos. 5,792,629, 5,407,915, 5,409,895, 7,019,123, and 6,583,108. The concept of fusion proteins of ulinastatin (and variations thereof) has been disclosed U.S. 20080181892, U.S. Pat. No. 5,541,288, and U.S. 20080255025. Certain UTI fusion proteins are described in CN 103044554A. The fusion proteins of CN 103044554A relate to specific variants in the Fc domain, presumably to avoid any Fc mediated pharmacological effects (ADCC, CDC). We have surprisingly found that a UTI-Fc with wild type IgG1 is well tolerated and provides significant increase in half-life. Also, compared to the UTI fusion proteins of CN 103044554A the present UTI fusion proteins, in particular SEQ ID NO:1, demonstrate greater thermal stability.

The present invention provides UTI fusion proteins, pharmaceutical compositions comprising the same, preparation methods, and uses thereof.

SUMMARY OF THE INVENTION

The present invention provides UTI fusion proteins, comprising a UTI domain and fusion partner wherein the UTI domain is operatively linked to the fusion partner. The present invention provides UTI fusion proteins, comprising a UTI domain and an Fc domain wherein the UTI domain is operatively linked to the Fc domain. The present invention also provides isolated UTI fusion proteins as described herein.

In some embodiments the present invention provides a UTI fusion protein, comprising a sequence comprising SEQ ID NO: 1, 3, 5, 7, 9, 11, 13, 15, 17, 19, 21, 23, 25, 27, and 29. In one embodiment, the present invention provides a UTI fusion protein comprising SEQ ID NO:1. In one embodiment, the present invention provides a UTI fusion protein comprising SEQ ID NO:3. In one embodiment, the present invention provides a UTI fusion protein comprising SEQ ID NO:5. In one embodiment, the present invention provides a UTI fusion protein comprising SEQ ID NO:7. In one embodiment, the present invention provides a UTI fusion protein comprising SEQ ID NO:9. In one embodiment, the present invention provides a UTI fusion protein comprising SEQ ID NO:11. In one embodiment, the present invention provides a UTI fusion protein comprising SEQ ID NO:13. In one embodiment, the present invention provides a UTI fusion protein comprising SEQ ID NO:15. In one embodiment, the present invention provides a UTI fusion protein comprising SEQ ID NO:17. In one embodiment, the present invention provides a UTI fusion protein comprising SEQ ID NO:19. In one embodiment, the present invention provides a UTI fusion protein comprising SEQ ID NO:21. In one embodiment, the present invention provides a UTI fusion protein comprising SEQ ID NO:23. In one embodiment, the present invention provides a UTI fusion protein comprising SEQ ID NO:25. In one embodiment, the present invention provides a UTI fusion protein comprising SEQ ID NO:27. In one embodiment, the present invention provides a UTI fusion protein comprising SEQ ID NO:29.

According to another embodiment of the present invention, the present invention provides a nucleic acid sequence encoding the UTI fusion proteins comprising the UTI fusion proteins described herein. Further, the invention provides the DNA sequences set forth as SEQ ID NO:2, 4, 6, 8, 10, 12, 14, 16, 18, 20, 22, 24, 26, 28, and 30. In one embodiment, the nucleic acid encoding a UTI fusion protein further comprises a vector containing control sequences to which the nucleic acid is operably linked. In another embodiment, the present invention provides a host cell comprising a nucleic acid sequence that encodes the UTI fusion protein, such as a mammalian, insect, *E. coli* or yeast cell, and maintaining the host cell under conditions in which the fusion protein molecule is expressed.

In another embodiment, the present invention provides a pharmaceutical composition comprising the UTI fusion proteins described herein and a pharmaceutically acceptable carrier or excipient.

According to a further embodiment of the present invention, there is provided a method of treating UTI-related disorders, comprising administering to a patient in need thereof an effective amount of a UTI fusion protein described herein.

That is, the present invention provides for the use of a UTI fusion protein as a medicament, including the manufacture of a medicament, and the use of a UTI fusion protein described herein for the treatment of the UTI-related disorders described herein.

BRIEF DESCRIPTION OF THE DRAWINGS

FIG. 7 Supression of protease activity (multiple proteases) by UTI-Fc1, UFC1, SEQ ID NO:1.

FIG. 9 Purification yields of UTI fusion proteins.

DETAILED DESCRIPTION OF THE INVENTION

Figure 1:
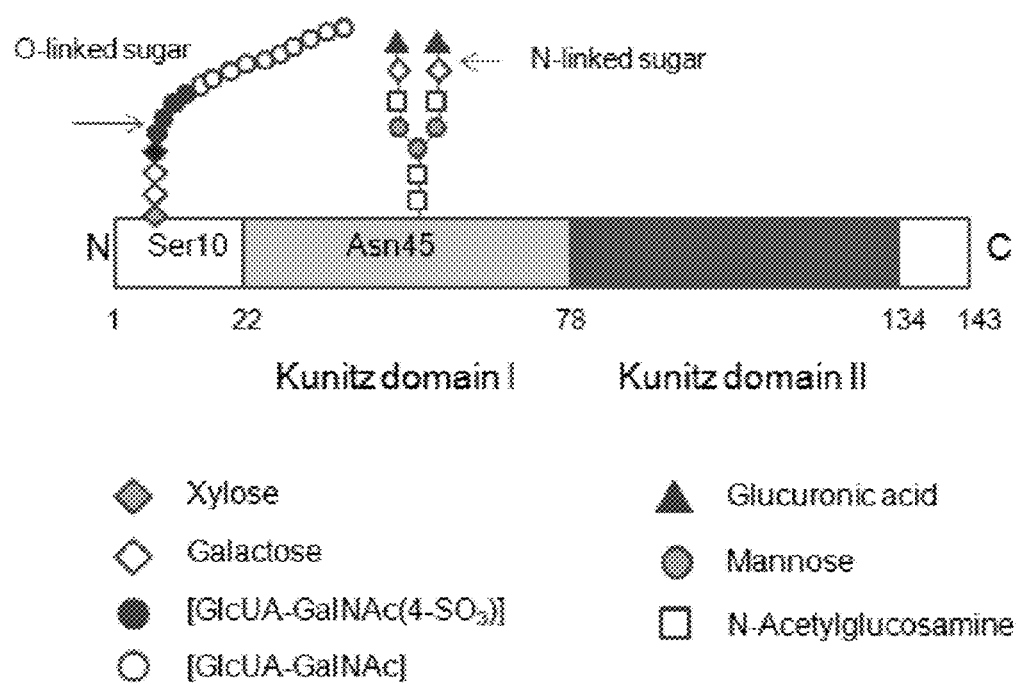
FIG. 1 UTI domain structure and glycosylation sites.

The present invention provides UTI fusion proteins, a UTI domain and fusion partner wherein the UTI domain is operatively linked to the fusion partner. The UTI fusion proteins of the present invention have an inhibitory effect on proteases, including trypsin.

In some embodiments the fusion partner is an Fc polypeptide. In some embodiments the fusion partner is a human Fc polypeptide. In some embodiments the fusion partner is analog(s) of human Fc polypeptide. In some embodiments the fusion partner is fragment(s) of human Fc polypeptide. In other embodiments the the fusion partner is a mouse Fc polypeptide. In other embodiments the the fusion partner is a rat Fc polypeptide.

In some embodiments the fusion partner is human albumin. In some embodiments the fusion partner is an analog of human albumin. In some emdiments the fusion partner is a modified human albumin. In some embodiments the fusion partner is a fragment of human albumin.

In some embodiments the UTI domain is human UTI (hUTI). In some embodiments the UTI domain is an analog of hUTI. In some embodiments the UTI domain is a fragment of hUTI. In some embodiments, the UTI fusion protein comprises a wild-type hUTI domain.

In some embodiments, the UTI fusion protein comprises a wild-type humanUTI domain and a human Fc domain. In some embodiments, the UTI fusion protein comprises a wild-type hUTI domain, and a linker domain, and a human Fc domain.

In some embodiments, the UTI fusion protein comprises awild-type humanUTI domain and a human albumin or analog thereof or fragment thereof. In some embodiments, the UTI fusion protein comprises wild-type hUTI domain, a linker domain, and a human albumin or analog thereof or fragment thereof.

In some embodiments, the Fc domain binds to an Fc receptor on a human cell. In some embodiments, the serum half-life of the molecule is significantly longer than the serum half-life of the UTI domain alone. In some embodiments, the protease inhibitory activity of the UTI domain of the molecule is the same or greater than the UTI domain alone. In some embodiments, administration of the molecule to a mouse decreases inflammatory reactions, including, but not limited to, decreasing the activation of immune cells or decreasing the production, secretion or activity of cytokines or chemokines.

It is understood that the UTI domain may be operatively linked to the fusion partner by a linker domain.

The present invention provides a UTI fusion protein, comprising a UTI domain fused to a polypeptide selected from the group consisting of a) Fc domain, b) an analog of the Fc domain, and c) fragment of the Fc domain wherein the UTI domain is fused to the Fc domain, analog thereof, or fragment thereof by a linker domain. The present invention provides a UTI fusion protein, comprising a hUTI domain fused to a polypeptide selected from the group consisting of a) Fc domain, b) an analog of the Fc domain, and c) fragment of the Fc domain wherein the hUTI domain is fused to the Fc domain, analog thereof, or fragment thereof by a linker domain.

The present fusion proteins encompass proteins having monomeric and multimeric forms whether prepared by a digest of an intact antibody or produced by other means.

The terms 'multimer" and "multimeric" refers to proteins in which Fc domains or molecules comprising Fc domains have two or more polypeptide chains associated covalently, non-covalently, or having both covalent and non-covalent interactions. The term multimer includes the term dimer.

The term "dimer" refers to proteins in which Fc domains or molecules comprising Fc domains have two polypeptide chains associated covalently, non-covalently, or having both covalent and non-covalent interactions. That is, the term "dimer" refers to UTI fusion proteins in which two Fc domains are associated covalently, non-covalently, or having both covalent and non-covalent interactions. More specifically, the term "dimer" refers to UTI fusion proteins in which two Fc domains are associated covalently.

The present invention provides a UTI fusion protein, comprising a UTI domain fused to a polypeptide selected from the group consisting of a) albumin, b) albumin analogs, c) fragments of albumin. The present invention also provides a UTI fusion protein, comprising a hUTI domain is fused to a polypeptide selected from the group consisting of a) human albumin, b) albumin analogs, c) fragments of human albumin wherein the hUTI is fused to the albumin, analog thereof, or fragment thereof by a linker domain.

DEFINITION OF TERMS

The terms used in this specification and claims are defined as set forth below unless otherwise indicated.

As used herein, the terms "linked," "fused," or "fusion" are used interchangeably.

These terms refer to the joining together of two more elements or components or domains, by whatever means including chemical conjugation or recombinant means. Methods of chemical conjugation are known in the art.

A "fusion protein" refers to a polypeptide having two or more portions covalently linked together, where one or more of the portions is derived from different proteins. The two portions may be linked directly by a single peptide bond (e.g., the portions linked directly to each other) or through a peptide linker containing one or more amino acid residues (e.g. with an intervening amino acid or amino acid sequence between the portions). Generally, DNA encoding the two portions and the linker will be in reading frame with each other and are produced using recombinant techniques.

A "UTI domain" is a protein or peptide that mimics the activity of UTI. It is understood that the UTI domain of the present invention may be altered such that they vary sequences from the naturally occurring or native sequences from which they were derived, while retaining the desired activity of the native sequence. Preferable the UTI domain is native humanUTI (hUTI), analogs, and variants thereof. Variants of hUTI include replacing or modifying one or more amino acids of native hUTI that are not a required structural feature or provide functional activity, including conservative substitutions. Variants of hUTI include removing or inserting one or more amino acids in native hUTI that are not a required structural feature or provide functional activity. Variants of hUTI include replacing or modifying one or more amino acids of native hUTI to modify one or more properties or activities. Variants of hUTI include removing or inserting one or more amino acids in native hUTI to modify one or more UTI properties or activities. Variants of hUTI include removing or altering glycolsyation sites in native humanUTI. Variants of hUTI include removing or altering one or more Kunitz domain. Variants of hUTI can be introduced by standard techniques, such as site-directed mutagenesis and PCR-mediated mutagenesis.

The amino acid residue sequence of the recombinant hUTI domain is set forth as SEQ ID NO:31. Generally, the UTI domain includes a sequence at least 80%, 81%, 82%, 83%, 84%, 85%, 86%, 87%, 88%, 89%, 90%, 91%, 92%, 93%, 94%, 95%, 96%, 97%, 98%, or 99% identical to the recombinant hUTI domain is set forth as SEQ ID NO:31.

An "Fc domain" is the polypeptide comprising the constant region of an antibody excluding the first constant region immunoglobulin domain and in some cases, part or all of the hinge. Thus, an Fc domain refers to the non-antigen binding portion of an antibody, whether in monomeric or multimeric form. The antibody from which the Fc domain arises is preferably of human origin and may be any of the immunogobulins, although IgG1 and IgG2 are preferred.

An Fc domain includes the hinge region of the heavy chain. By "hinge" or "hinge region" or "antibody hinge region" or "immunoglobulin hinge region" herein is meant the flexible polypeptide comprising the amino acids between the first and second constant domains of an antibody, just upstream of the papian cleavage. Accordingly, for IgG, an Fc domain comprises immunoglobulin domains CH2 and CH3 and the hinge region between CH1 and CH2. Although the boundaries of the Fc region may vary, the human IgG heavy chain Fc region is usually defined to include residues C226 or P230 to its carboxyl-terminus, wherein the numbering is according to the EU index and in Kabat. In some embodiments, as is more fully described below, amino acid modifications are made to the Fc domain, for example to alter binding to one or more FcγR receptors or to the FcRn receptor.

Accordingly, in certain embodiments, the term Fc domain includes the hinge region which may be truncated, modified by replacement, deletion and/or insertion and further the modified or unmodified hinge region may be the site of attachment of a linker domain.

An "analog of an Fc domain" refers to a molecule or sequence that is modified from the native Fc but still comprises a binding site for the salvage receptor. The term analog of an Fc domain includes a molecule or sequence that is humanized from a non-human native Fc. The term analog of an Fc domain also includes a molecule or sequence that lacks, or has modifications of, one or more native Fc residues that affect or are involved in disulfide formation, incompatibility with a host cell, N-terminal heterogeneity upon expression, stability, glycolsyation, interaction with a complement, binding to an Fc salvage receptor and/or interaction with an Fcγ receptor.

The terms "fragments of the Fc domain" or "fragment of the Fc domain" refers to a native Fc from which one or more sites have been removed where the removed site(s) does not constitute structural features or functional activity that is required by the fusion proteins of the present invention. Fragments of the Fc domain include deleting residues from the native Fc or truncating the native Fc and may include substitutions of the remaining residues. The inserted or altered residues (e.g., the substituted residues) may be natural amino acids or altered amino acids, peptidomimetics, unnatural amino acids, or D-amino acids.

Generally, the Fc domain includes a sequence at least 80%, 81%, 82%, 83%, 84%, 85%, 86%, 87%, 88%, 89%, 90%, 91%, 92%, 93%, 94%, 95%, 96%, 97%, 98%, or 99% identical to IgG1, IgG2, IgG3, IgG4, IgD, IgA, IgE, or IgM, in particular human IgG1 or IgG2.

The term Fc domain encompasses native Fc and analogs of Fc and includes monomeric and multimeric forms whether prepared by a digest of an intact antibody or produced by other means.

In certain embodiments, an Fc domain comprises at least a hinge domain (upper, middle, and/or lower hinge region), a CH2 domain (or a variant or fragment thereof), and a CH3 domain (or a variant or fragment thereof). In another embodiment, an Fc domain consists of a hinge domain (upper, middle, and/or lower hinge region), a CH2 domain (or a variant or fragment thereof), and a CH3 domain (or a variant or fragment thereof). In certain other embodiments, an Fc domain consists of a hinge domain (upper, middle, and/or lower hinge region), a CH2 domain (or a variant or fragment thereof), a CH3 domain (or a variant or fragment thereof), and a CH4 domain (or a variant or fragment thereof). In another embodiment, an Fc domain consists of a hinge domain (upper, middle, and/or lower hinge region) and a CH2 domain. In another embodiment, an Fc domain consists of a hinge domain (upper, middle, and/or lower hinge region) and a CH3 domain (or a variant or fragment thereof). In another embodiment, an Fc domain consists of a CH2 domain (or a variant or fragment thereof), and a CH3 domain (or a variant or fragment thereof). In another embodiment, an Fc domain consists of a complete CH2 domain and a complete CH3 domain. In another embodiment, an Fc domain consists of a complete CH2 domain and a complete CH3 domain. In one embodiment, an Fc domain of the invention comprises at least the portion of an Fc molecule known in the art to be required for FcRn binding. In another embodiment, an Fc domain of the invention comprises at least the portion of an Fc molecule known in the art to be required for Protein A binding. In another embodiment, an Fc domain of the invention comprises at least the portion of an Fc molecule known in the art to be required for Protein G binding.

According to the present invention, an Fc domain generally refers to a polypeptide comprising all or part of the Fc domain of an immunoglobulin heavy-chain. As discussed above, this includes, but is not limited to polypeptides comprising the entire hinge region, CH1, CH2, and/or CH3 domains as well as fragments of such peptides comprising, for example, the hinge, CH2 and CH3 domains. The Fc domain may be derived from any immunoglobulin of any species and/or subtype, including but not limited to, a human IgG1, IgG2, IgG3, IgG4, IgD, IgA, IgE, or IgM antibody. An Fc domain includes the last two constant region immunoglobulin domains of IgA, IgD, and IgG, the last three constant region immunoglobulin domains of IgE and IgM, and the flexible hinge N-terminal to these domains. For IgA and IgM, Fc may include the J chain.

An Fc domain as used herein encompasses native Fc and Fc variant molecules. As with the Fc variants and native Fc proteins, the term Fc domain includes molecules in monomeric and multimeric form, whether digested from an antibody or produced by other means.

As set forth herein it is understood, that any Fc domain may be modified such that it varies in amino acid sequence from the native Fc domain of a naturally occurring immunoglobulin molecule. In certain exemplary embodiments, the Fc domain retains an effector function, for example, FcγR binding. In certain exemplary embodiments, the Fc domain lacks an effector function, for example, FcγR binding.

The Fc domain of the invention may be derived from different immunoglobulin molecules. For example, an Fc domain may comprise a CH2 and/or CH3 domain derived from IgG1 and hinge region derived from IgG3.

In some embodiments, UTI fusion proteins include an Fc domain. Fc domains useful for producing the UTI fusion proteins of the present invention may be obtained from a number of different sources. In preferred embodiments, an Fc domain of the UTI fusion proteins is derived from a human immunoglobulin. It is understood, however, that the Fc domain may be derived from an immunoglobulin of another mammalian species, including for example, a rodent (e.g. a mouse, rat, rabbit, guinea pig) or non-human primate (e.g. Chimpanzee, Macaque) species. Moreover, the UTI fusion proteins Fc domain or portion thereof may be derived from any immunoglobulin class.

The terms "wild-type" or "wt" or "native" as used herein is meant an amino acid sequence or a nucleotide sequence that is found in nature, including allelic variations. A wild-type protein, polypeptide, antibody, immunoglobulin, IgG, polynucleotide, DNA, RNA, and the like has an amino acid sequence or a nucleotide sequence that has not been intentionally modified.

In certain embodiments the UTI fusion proteins of the present invention can employ a linker domain. The linker domain is used to operationally connect a UTI domain to a fusion partner.

The term "linker domain" refers to polypeptide linkers, non-peptide linkers and combinations thereof. In particular, a linker domain can be a polypeptide. As used herein, the term "linker domain" refers to a sequence which connects two domains in a linear sequence. As used herein, the term "polypeptide linker" refers to a peptide or polypeptide sequence (e.g., a synthetic peptide or polypeptide sequence) which connects two domains in a linear amino acid sequence of a polypeptide chain. For example, polypeptide linkers may be used to connect a UTI domain to an Fc domain. Preferably, such polypeptide linkers can provide flexibility to the polypeptide molecule. A UTI fusion protein of the invention may comprise a linker domain, including a peptide linker.

For example, a linker domain can be used to connect two domains in a linear amino acid sequence of a polypeptide linker, such as linking a UTI domain with an Fc domain. In certain embodiments a linker domain can be used to connect a UTI domain to a Fc domain. The linker domain can be used to connect the domains in any order. For example, in some embodiments a linker will connect a UTI domain and an Fc domain with the order UTI-linker-Fc, whereas in other embodiments a linker will connect a UTI domain and an Fc domain with the order Fc-linker-UTI, where the polypeptide regions are denoted from N-terminus to C-terminus. Exemplary polypeptide linkers include those that consist of glycine and serine residues, the so-called Gly-Ser polypeptide linkers. As used herein, the term "Gly-Ser polypeptide linker" refers to a peptide that consists of glycine and serine residues. An exemplary Gly-Ser polypeptide linker comprises the amino acid sequence Ser(Gly$_4$Ser)$_n$ wherein n is an integer 1 to 10, SEQ ID NO:33-42, respectively. In one embodiment, the UTI fusion protein includes one or two Gly-Ser polypeptide linker(s) in which n=1. In one embodiment, the UTI fusion protein includes one or two Gly-Ser polypeptide linker(s) in which n=2. In one embodiment, the UTI fusion protein includes one or two Gly-Ser polypeptide linker(s) in which n=3. In one embodiment, the UTI fusion protein includes one or two Gly-Ser polypeptide linker(s) in which n=4. In one embodiment, the UTI fusion protein includes one or two Gly-Ser polypeptide linker(s) in which n=5. In one embodiment, the UTI fusion protein includes one or two Gly-Ser polypeptide linker(s) in which n=6. In one embodiment, the UTI fusion protein includes one or two Gly-Ser polypeptide linker(s) in which n=7. In one embodiment, the UTI fusion protein includes one or two Gly-Ser polypeptide linker(s) in which n=8. In one embodiment, the UTI fusion protein includes one or two Gly-Ser polypeptide linker(s) in which n=9. In one embodiment, the UTI fusion protein includes one or two Gly-Ser polypeptide linker(s) in which n=10.

Another exemplary linker is given in SEQ ID NO:43.

The term "comprising" means that a compound, i.e., fusion protein, may include additional amino acids on either or both the N- or C-termini. Of course, these additional amino acids should not significantly interfere with the activity of the compound, i.e., fusion protein.

The term "amino acid" refers to naturally occurring and synthetic amino acids as well as amino acid analogs and amino acid mimetics that function in a manner similar to naturally occurring amino acids. Naturally occurring amino acids are those encoded by the genetic code, as well as those encoded amino acids which are later modified, for example, hydroxyproline and phosphoserine. Amino acid analogs refer to compound, i.e., fusion proteins that have the same basic chemical structure as the naturally occurring amino acids, that is, a carbon atom bound to a hydrogen atom, carboxyl group, an amino group, and an R group. Amino acid analogs have modified R groups, or give rise to modified peptide backbones, but retain the same basic chemical structure as the naturally occurring amino acids.

The term "amino acid substitution" refers to the replacement of at least one existing amino acid residue in a predetermined or native amino acid sequence with a different "replacement" amino acid.

The term "amino acid insertion" refers to the insertion of one or more additional amino acids into a predetermined or native amino acid sequence. The insertion can be one, two, three, four, five, or up to twenty amino acid residues.

The term "amino acid deletion" refers to removal of at least one amino acid from a predetermined or native amino acid sequence. The deletion can be one, two, three, four, five, or up to twenty amino acid residues.

The terms "polypeptide," "peptide," and "protein" are used interchangeably herein and refer to a polymer of amino acid residues. The terms apply to amino acid polymers in which one or more amino acid is a non-natural amino acid, synthetic amino acid, or amino acid mimetic.

The term "nucleic acid" refers to a deoxyribonucleotide or ribonucleotide and polymers thereof in either single strand or double strand form. The term "nucleic acid" is used interchangeably with gene, nucleotide, polynucleotide, cDNA, DNA, and mRNA. Unless specifically limited the term encompasses nucleic acids containing known analogues of natural nucleotides that have similar binding propertied as the natural nucleic acid. Unless specifically limited, a particular nucleotide sequence also encompasses conservatively modified variants thereof (for example, those containing degenerate codon substitutions) and complementary sequences as well as the as well as the sequences specifically described.

The polynucleotides of the present invention can be composed of any polyribonucleotide or polydeoxyribonucleotide, which can be unmodified RNA or DNA or modified RNA or DNA. For example, polynucleotides can be composed of single or double stranded regions, mixed single or double stranded regions. In addition, the polynucleotides can be triple stranded regions containing RNA or DNA or both RNA and DNA. Modified polynucleotides include modified bases, such as tritylated bases or unusual bases such as inosine. A variety of modification can be made to RNA and DNA, thus polynucleotide includes chemically, enzymactically, or metabolically modified forms.

The term "derivatized" or derivative" refers to compound, i.e., fusion proteins that have a cyclic portion, for example, cross-linked between cysteinyl residues, the compound, i.e., fusion protein, is cross-linked, one or more peptidyl linkages is replaced by a non-peptide linkage, or the N-terminus is replaced by a $NRR_1$, $NRC(O)R_1$, $NRC(O)OR_1$, $NHC(O)NHR_1$, $NRS(O)_2R_2$, succinamide or other group wherein R and $R_1$ are defined herein and/or the C-terminus is replaced with $C(O)R_3$ or $NR_4R_5$, and compound, i.e., fusion proteins in which amino acid moieties are modified by treatment with agents capable of reacting with selected side chains or terminal residues. R is selected from the group consisting of hydrogen and $C_{1-6}$ alkyl, $R_1$ is selected from the group consisting of hydrogen and $C_{1-6}$ alkyl, $R_2$ is selected from the group consisting of $C_{1-6}$ alkyl, $C_{3-8}$ cycloalkyl, and optionally substituted phenyl; $R_3$ is selected from the group consisting of hydrogen, $C_{1-6}$ alkyl, and $C_{3-8}$ cycloalkyl; $R_4$ is selected from the group consisting of hydrogen and $C_{1-6}$ alkyl; $R_5$ is selected from the group consisting of hydrogen, $C_{1-6}$ alkyl and $C_{3-8}$ cycloalkyl; or $R_4$ and $R_5$ are taken together with the nitrogen to which they are attached form a 4 to 7 membered, saturated, ring optionally having 1 additional ring heteroatom selected from the group N, O, and S.

The term "$C_{1-6}$ alkyl" refers to a straight or branched alkyl chain of one to six carbon atoms.

The term "$C_{3-8}$ cycloalkyl" refers to monocyclic or bicyclic, saturated or partially (but not fully) unsaturated alkyl ring of three to eight carbon atoms, and includes cyclopropyl, cyclobutyl, cyclopentyl, cyclohexyl, and the like. It is understood that the term includes benzofused cyclopentyl and cyclohexyl.

The term "optionally substituted phenyl" refers to a phenyl group optionally substituted with 1 to 3 substituents independently selected from the group consisting of halo, $C_{1-6}$ alkyl, $C_{1-6}$ alkoxy, cyano, and trifluoromethyl.

Preparation

The compounds, i.e., fusion proteins, of this invention may be prepared by standard synthetic methods, recombinant DNA techniques, or other methods of preparing peptides and fusion proteins. In an exemplary process a hUTI domain is covalently linked to an Fc domain by expression of a DNA construct encoding the UTI domain and the Fc domain and any linker domain.

Alternative ways to construct a UTI fusion protein are envisioned. In some embodiments, the domain orientation can be altered to construct an Fc-UTI molecule or a UTI-Fc molecule or a UTI-Fc-UTI molecule that retains FcR binding and has active UTI domain.

In some embodiments, UTI fusion proteins include a wild-type Fc domain that can allow the fusion protein to undergo endocytosis after binding FcRn (Fc neonatal receptor). Thus, the present invention further provides methods for producing the disclosed UTI fusion proteins. These methods encompass culturing a host cell containing isolated nucleic acid(s) encoding the UTI fusion proteins of the invention. As will be appreciated by those in the art, this can be done in a variety of ways, depending on the nature of the UTI fusion protein. In some embodiments, the UTI fusion protein of the invention is produced and can be isolated.

In general, nucleic acids are provided that encode for the UTI fusion protein of the invention. Such polynucleotides encode for a UTI domain, the fusion partner, and any linker domain. The present invention also contemplates oligonucleotide fragments derived from the disclosed polynucleotides and nucleic acid sequences complementary to these polynucleotides.

The polynucleotides can be in the form of RNA or DNA. Polynucleotides in the form of DNA, cDNA, genomic DNA, nucleic acid analogs, and synthetic DNA are within the scope of the present invention. The DNA may be double-stranded or single-stranded, and if single stranded, may be the coding (sense) strand or non-coding (anti-sense) strand. The coding sequence that encodes the polypeptide may be identical to the coding sequence provided herein or may be a different coding sequence, which sequence, as a result of the redundancy or degeneracy of the genetic code, encodes the same polypeptides as the DNA provided herein.

In some embodiments, nucleic acid(s) encoding the UTI fusion proteins of the invention are incorporated into expression vectors, which can be extrachromosomal or designed to integrate into the genome of the host cell into which it is introduced. Expression vectors can contain any number of appropriate regulatory sequences (including, but not limited to, transcriptional and translational control sequences, promoters, ribosomal binding sites, enhancers, origins of replication, etc.) or other components (selection genes, etc.), all of which are operably linked as is well known in the art. In some cases two nucleic acids are used and each put into a different expression vector (e.g. heavy chain in a first expression vector, light chain in a second expression vector), or alternatively they can be put in the same expression vector. It will be appreciated by those skilled in the art that the design of the expression vector(s), including the selection of regulatory sequences may depend on such factors as the choice of the host cell, the level of expression of protein desired, etc.

In general, the nucleic acids and/or expression can be introduced into a suitable host cell to create a recombinant host cell using any method appropriate to the host cell selected (e.g., transformation, transfection, electroporation, infection), such that the nucleic acid molecule(s) are operably linked to one or more expression control elements (e.g., in a vector, in a construct created by processes in the cell, integrated into the host cell genome). The resulting recombinant host cell can be maintained under conditions suitable for expression (e.g. in the presence of an inducer, in a suitable non-human animal, in suitable culture media supplemented with appropriate salts, growth factors, antibiotics, nutritional supplements, etc.), whereby the encoded polypeptide(s) are produced. In some cases, the heavy chains are produced in one cell and the light chain in another.

Mammalian cell lines available as hosts for expression are known in the art and include many immortalized cell lines available from the American Type Culture Collection (ATCC), Manassas, Va. including but not limited to Chinese hamster ovary (CHO) cells, HEK 293 cells, NSO cells, HeLa cells, baby hamster kidney (BHK) cells, monkey kidney cells (COS), human hepatocellular carcinoma cells (e.g., Hep G2), and a number of other cell lines. Non-mammalian cells including but not limited to bacterial, yeast, insect, and plants can also be used to express recombinant antibodies. In some embodiments, the antibodies can be produced in transgenic animals such as cows or chickens.

In an embodiment, the fusion proteins of the invention are encoded by a nucleotide sequence. Nucleotide sequences of the invention can be useful for a number of applications, including: cloning, gene therapy, protein expression and purification, mutation introduction, DNA vaccination of a host in need thereof, antibody generation for, e.g., passive immunization, PCR, primer and probe generation, siRNA design and generation and the like. In an embodiment, the nucleotide sequence of the invention comprises, consists of, or consists essentially of, a nucleotide sequence selected from SEQ ID NO:2, 4, 6, 8, 10, 12, 14, 16, 18, 20, 22, 24, 26, 28, 30, or 32.

In an embodiment, a nucleotide sequence includes a nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a nucleotide sequence set forth in SEQ ID NO:2, 4, 6, 8, 10, 12, 14, 16, 18, 20, 22, 24, 26, 28, 30, or 32. In an embodiment, a nucleotide sequence includes a contiguous nucleotide sequence at least 80%, 81%, 82%, 83%, 84%, 85%, 86%, 87%, 88%, 89%, 90%, 91%, 92%, 93%, 94%, 95%, 96%, 97%, 98%, or 99% identical to a contiguous nucleotide sequence set forth in SEQ ID NO:2, 4, 6, 8, 10, 12, 14, 16, 18, 20, 22, 24, 26, 28, 30, or 32.

Preferred UTI fusion proteins of the invention comprise a sequence (e.g., at least one Fc domain) derived from a human immunoglobulin sequence. However, sequences may comprise one or more sequences from another mammalian species. For example, a primate Fc domain or nuclease domain may be included in the subject sequence. Alternatively, one or more murine amino acids may be present in a polypeptide. In some embodiments, polypeptide sequences of the invention are not immunogenic and/or have reduced immunogenicity. The UTI fusion proteins of the invention may comprise conservative amino acid substitutions at one or more amino acid residues, e.g., at essential or non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in a binding polypeptide is preferably replaced with another amino acid residue from the same side chain family. In another embodiment, a string of amino acids can be replaced with a structurally similar string that differs in order and/or composition of side chain family members. Alternatively, in another embodiment, mutations may be introduced randomly along all or part of a coding sequence, such as by saturation mutagenesis, and the resultant mutants can be incorporated into binding polypeptides of the invention and screened for their ability to bind to the desired target.

Uses

In one embodiment, the invention provides methods of diagnosing and treating UTI-related conditions. As used herein terms "condition," "disorder," and "disease" relate to any unhealthy or abnormal state. The term "UTI-related conditions" includes conditions, disorders, and diseases in which UTI provides a therapeutic benefit. The term "UTI-related conditions" include conditions characterized by an immunomodulatory or an inflammatory effect. In particular, the term UTI-related conditions include pancreatitis, including acute pancreatitis and chronic pancreatitis, systemic inflammatory response syndrome, acute circulatory failure (e.g., caused by shock), disseminated intravascular coagulation, and multiple organ dysfunction syndrome. The term UTI-related conditions also include use in high-risk surgical patients. The term UTI-related conditions also includes infections of the lung, liver, heart, or kidney. The term UTI-related conditions also includes severe sepsis. The term UTI-related conditions also includes acute lung injury (ALI) caused by SARS viruses or acute respiratory distress syndrome (ARDS).

In one embodiment, the invention provides methods of treating a UTI-related condition, comprising administering to a patient in need thereof an effective amount, e.g., a pharmaceutically effective amount, of a disclosed UTI fusion protein. In certain embodiments, the condition is one specifically mentioned herein.

The pharmaceutical compositions of the present invention are prepared in a manner well known in the pharmaceutical art and include at least one of UTI fusion protein of the invention as the active ingredient. Pharmaceutical composition of the UTI fusion proteins used in accordance with the present invention are prepared by mixing a UTI fusion protein having the desired degree of purity with optional pharmaceutically acceptable excipients. The term "pharmaceutically acceptable excipient" refers to those typically used in preparing pharmaceutical compositions and should be pharmaceutically pure and non-toxic in the amounts used. They generally are a solid, semi-solid, or liquid material which in the aggregate can serve as a vehicle or medium for the active ingredient. Some examples of pharmaceutically acceptable excipients are found in Remington's Pharmaceutical Sciences and the Handbook of Pharmaceutical Excipients and include diluents, vehicles, carriers, sustained release matrices, stabilizing agents, preservatives, solvents, suspending agents, buffers, emulsifiers, dyes, propellants, coating agents, and others. Generally for injection or intravenous administration the UTI fusion proteins of the present invention are in the form of lyophilized formulations, or aqueous solutions.

Pharmaceutically acceptable excipients are nontoxic to subjects in the amounts used, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The pharmaceutical compositions herein may also contain more than one active compound, i.e., fusion protein, as necessary for the particular indication being treated, preferably those with complementary activities that do not adversely affect each other. Such molecules are suitably present in combination in amounts that are effective for the purpose intended.

The pharmaceutical compositions to be used for in vivo administration should be sterile, or nearly so. This is readily accomplished by filtration through sterile filtration membranes.

The UTI fusion proteins of the invention are administered to a subject, in accord with known methods, such as intravenous administration as a bolus or by continuous infusion over a period of time, by intramuscular, intraperitoneal, intracerobrospinal, subcutaneous, intra-articular, intrasynovial, or intrathecal injection or infusion or by topical or inhalation routes. Intravenous or subcutaneous administration of the UTI fusion protein is preferred.

The terms "treat," "treatment," and "treating" include improvement of the conditions described herein. The terms "treat," "treatment," and "treating" include all processes providing slowing, interrupting, arresting, controlling, or stopping of the state or progression of the conditions described herein, but does not necessarily indicate a total elimination of all symptoms or a cure of the condition. The terms "treat," "treatment," and "treating" are intended to include therapeutic treatment of such disorders. The terms "treat," "treatment," and "treating" are intended to include prophylactic treatment of such disorders.

As used herein the terms "patient" and "subject" includes humans and non-human animals, for example, mammals, such as mice, rats, guinea pigs, dogs, cats, rabbits, cows, horses, sheep, goats, and pigs. The term also includes birds, fish, reptiles, amphibians, and the like. It is understood that a more particular patient is a human. Also, more particular patients and subjects are non-human mammals, such as mice, rats, and dogs.

As used herein, the term "effective amount" refers to the amount of compound, i.e., fusion protein, of the invention which treats, upon single or multiple dose administration, a patient suffering from the mentioned condition. An effective amount can be readily determined by the attending diagnostician as a medical professional, such as a physician or a veterinarian as one skilled in the art, by the use of known techniques and by observing results obtained under analogous circumstances. For example, a medical professional could start doses of the medicament employed in the pharmaceutical composition at levels lower than that required in order to achieve the desired therapeutic effect and gradually increase the dosage until the desired effect is achieved.

In determining the effective amount, the dose, a number of factors are considered by the attending diagnostician, including, but not limited to: the species of patient; its size, age, and general health; the specific condition, disorder, or disease involved; the degree of or involvement or the severity of the condition, disorder, or disease, the response of the individual patient; the particular compound, i.e., fusion protein, administered; the mode of administration; the bioavailability characteristics of the preparation administered; the dose regimen selected; the use of concomitant medication; and other relevant circumstances. Specific amounts can be determined by the skilled person. Although these dosages are based on an average human subject having a mass of about 60 kg to about 70 kg, the physician will be able to determine the appropriate dose for a patient (e.g., an infant) where the mass falls outside of this weight range.

Dosage regimens are adjusted to provide the desired response. For example, a single bolus may be administered, several divided doses may be administered over time or the dose may be proportionally reduced or increased as indicated by the exigencies of the therapeutic situation.

Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound, i.e., fusion protein, calculated to produce the desired therapeutic effect in association with the required pharmaceutical carrier.

The present pharmaceutical compositions are preferably formulated in a unit dose form, each dose typically containing from about 0.5 mg to about 100 mg of a UTI fusion protein of the invention. The term "unit dose form" refers to a physically discrete unit containing a predetermined quantity of active ingredient, in association with a suitable pharmaceutical excipient, by which one or more is used throughout the dosing regimen to produce the desired therapeutic effect. One or more "unit dose form" may be taken to affect the treatment dosage.

An exemplary, non-limiting range for an effective amount of a UTI fusion protein used in the present invention is about 0.1-100 mg/kg, such as about 0.1-50 mg/kg, for example about 0.1-20 mg/kg, such as about 0.1-10 mg/kg, for instance about 0.5 mg/kg, about such as 0.3 mg/kg, about 1 mg/kg, or about 3 mg/kg. In another embodiment, the UTI fusion protein is administered in a dose of 1 mg/kg or more, such as a dose of from 1 to 20 mg/kg, e.g. a dose of from 5 to 20 mg/kg, e.g. a dose of 8 mg/kg. An exemplary, non-limiting range for an effective amount of a UTI fusion protein used in the present invention is about 1-500 mg/dosage, such as about 1-100 mg/dosage, for example about 1-50 mg/dosage, such as about 1-10 mg/dosage, for instance about 1 mg/dosage, or about 3 mg/dosage, or about 5 mg/dosage. In one embodiment, the UTI fusion protein is administered by infusion in an every 3 days or weekly dosage of from 10 to 500 mg/dosage. Such administration may be repeated as necessary to maintain the desired therapeutic effect.

As non-limiting examples, treatment according to the present invention may be provided a dosage of UTI fusion protein in an amount of about 0.1-100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day; 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mg/kg, or alternatively, at least once a week 1, 2, 3, 4, 5, 6, 7, 8, 9, 10, 11, 12, 13, 14, 15, 16, 17, 18, 19 or 20 mg/kg after initiation of treatment, or any combination thereof. As non-limiting examples, treatment according to the present invention may be provided a dosage of UTI fusion protein in an amount of about 1-100 mg/dosage, such as 1, 5, 10, 20, 30, 40, 45, 50, 60, 70, 80, 90, 100 150, 200, 250, 300, 350, or 400 mg/dosage. On at least once a day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 mg/dosage after initiation of treatment, or any combination thereof. On at least one of week 1, 10, 20, 30, 40, 50, 60, 70, 80, 90, or 100 mg/dosage after initiation of treatment, or any combination thereof.

The UTI fusion proteins of the invention find use in a variety of applications, including treatment of UTI-related diseases. UTI fusion proteins of the invention may find use in treating diseases with immune system involvement, auto-immune diseases, inflammatory diseases, post-operative inflammatory responses, lysosome-associated diseases, coagulation diseases protease-related diseases and as an adjuvant therapy during surgery. UTI fusion proteins of the invention may find use in treating pancreatitis (including endoscopy-induced pancreatitis and acute pancreatitis), arthritis, SARS, systemic inflammatory response syndrome, acute circulatory failure, sepsis, hepatitis, appendicitis, colitis, organ failure, organ damage (including pancreas, kidney, lung), reperfusion injury, Stevens-Johnson syndrome, toxic epidermal necrolysis, shock, ischemic injuries, acute lung injury (including that caused by acute aortic dissection), asthma, lung inflammation, pneumonia (including ventilator-associated), disseminated intravascular coagulation (DIC), acute respiratory distress syndrome (ARDS), and systemic inflammatory response syndrome.

UTI fusion proteins of the present invention may find use in inhibiting proteases, including the serine proteases, including, trypsin, chymotrypsin, thrombin, kallikrein, plasmin, elastase, cathepsin, lipase, hyaluronidase, factors IXa, Xa, XIa, and XIIa, and polymorphonuclear leukocyte elastase.

UTI fusion proteins of the present invention may find use in suppression of proinflammatory mediators, such as cytokines, tumor necrosis factor-alpha, interleukin-1, -1β, -4, -6 and -8, -10 and chemokines.

UTI fusion proteins of the present invention may find use in treatment of cancer, including the prevention of tumor invasion and metastasis, altered rates of apoptosis, and reduction of loss of renal function in cisplatinum treatment.

UTI fusion proteins of the present invention may find use to treat AIDS, including as adjunctive treatment.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structure and Molecular Properties (W. H. Freeman and Company, 1993); A. L. Lehninger, Biochemistry (Worth Publishers, Inc.); Sambrook, et al, Molecular Cloning: A Laboratory Manual (2nd Edition, 1989); Methods In Enzymology (S. Colowlck and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B (1992).

Example 1

Construction of DNA Vectors Encoding UTI Fusion Proteins.

Methods for performing molecular biology are known in the art and can be found, for example, in Molecular Cloning: A laboratory Manual 4th edition (Micheal Green and Joseph Sambrook, Cold Spring Harbor Press, 2012).

A gene encoding UTI-Fc1 was ordered using the GeneArt codon-optimized gene synthesis services from Life Technologies (Carlsbad, Calif.). The protein sequence is as listed in SEQ ID NO: 1 with a signal peptide, MGWSCIILFL-VATATGVHS (SEQ ID NO:44), added for secretion. Figure shows the general regions of UTI used in the fusion. The gene encoding UTI-Fc1 was ligated into a mammalian expression vector. Mammalian expression vectors are known in the art including pSecTag2/Hygro A, pcDNA4 and pcDNA6 vectors (Life Technologies, Carlsbad Calif.). The vector was digested with the restriction enzymes, HindIII-HF and EcoRI from New England Biolabs (NEB). This fragment was ligated into the expression vector which provides carbenicillin resistance and had been digested with the same two restriction enzymes. A vector: insert molar ratio of 1:3 was used in ligation. Ligated DNA was transformed into 10-beta chemically competent E. coli cells from NEB, and plated on LB-Carbenicillin plates for overnight growth. Colonies were grown overnight in LB with Carbenicillin and miniprep DNA was prepared by Qiagen's QIAprep Spin Miniprep Kit (Qiagen, Hilden, Germany). DNA was then sequenced using DNA sequencing services from Bio Applied Technologies Joint (BATJ, San Diego). The sequence verified colony was subsequently grown in LB media with carbenicillin for DNA purification with the BenchPro 2100 instrument and MaxiCard from Life Technologies.

Example 2

Construction of DNA Vectors Encoding Variants of UTI-Fc Fusion Proteins

Figure 2:
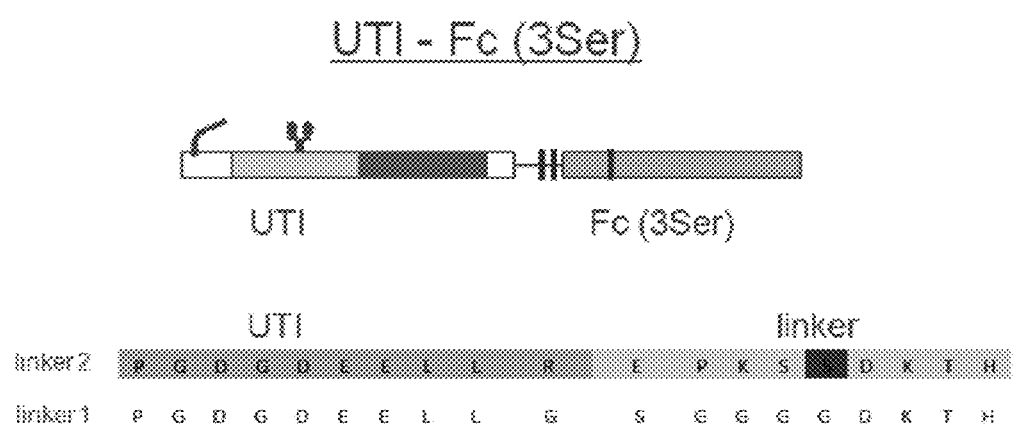
FIG. 2 Two UTI-Fc constructs demonstrating altered linkers. Shown are the amino acid sequences corresponding to amino acid residues 135-153 of SEQ ID NO: 3 (top, linker 2) and SEQ ID NO: 1 (bottom, linker 1).
Figure 3:
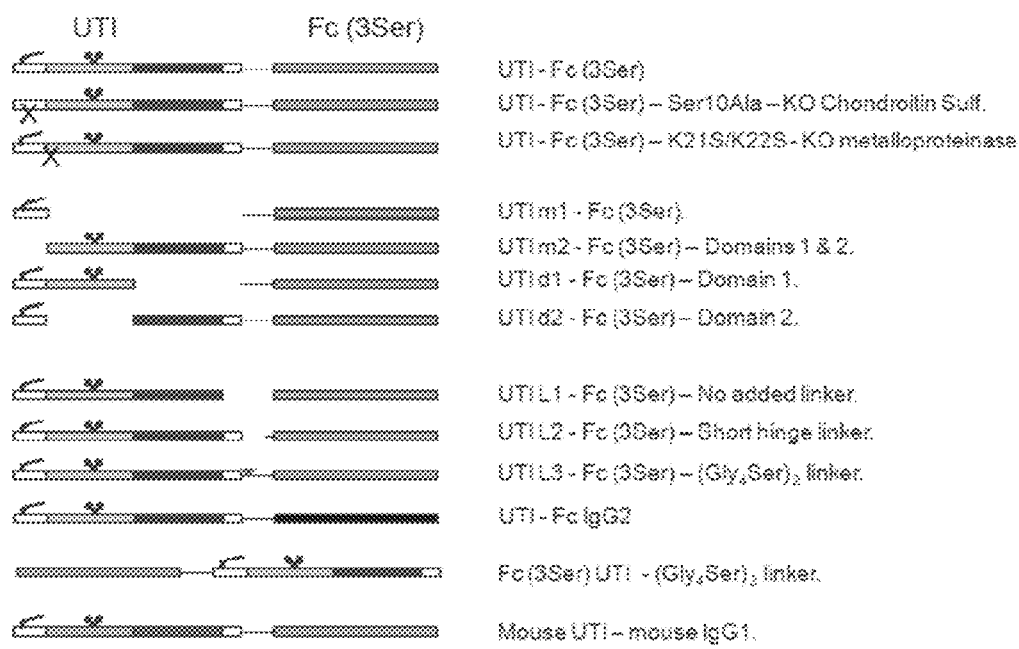
FIG. 3 Various UTI-Fc constructs of the present invention.

SEQ ID NOS:1-28 list DNA and protein sequences of some UTI-Fc fusion proteins. These UTI fusion proteins comprise modifications that alter Ig isotype, linkers, UTI domain, UTI and Fc domain order (N- or C-termimal), UTI species, Fc species, UTI start/stop residues, sugar attachment, protease sensitive sites, and Fc effector function. Some UTI-Fc proteins are depicted in FIGS. 2 and 3. UTI-Fc fusion proteins comprising three amino acid modifications to Ser (IgG1 Fc3Ser, C154S/P172S/P265S) comprises mutations to alter disulfide bond formation and FcγR functions.

Creation of UTI-Fc Expression Constructs

Figure 4:
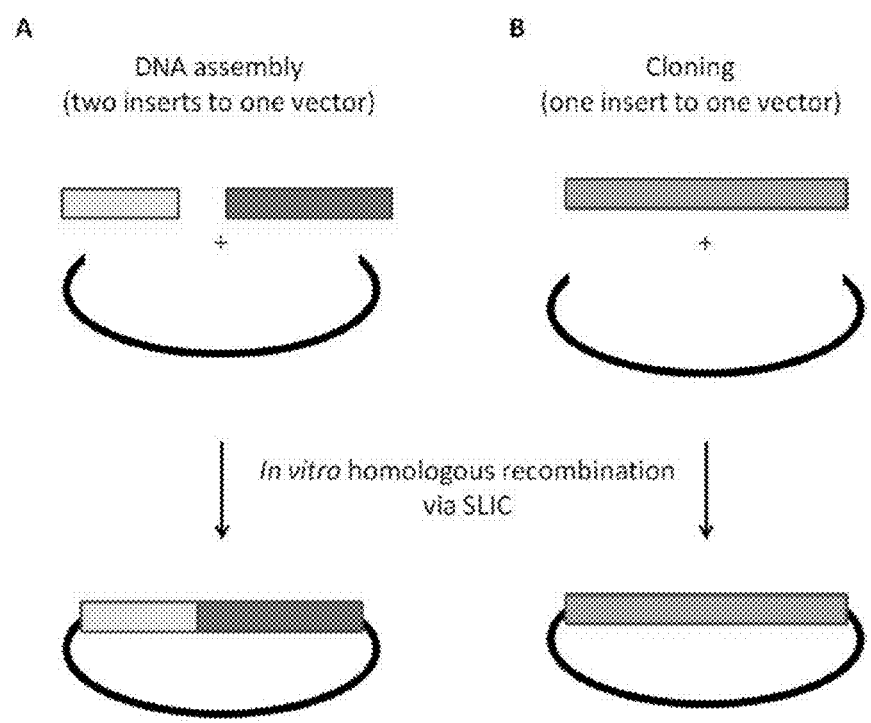
FIG. 4 DNA assemble strategy (SLIC) used in UTI fusion construction.

The nucleotide sequences of the UTI (e.g. wild-type, S10A, and K21S K22S variants) and human Fc3Ser domains were codon optimized for CHO cell expression and synthesized by Life Technologies (Carlsbad, Calif.). The following constructs were created in a CHO expression vector by assembling UTI and Fc3Ser domains via sequence and ligation-independent cloning (SLIC) method (Li and Elledge 2007 Nature Methods 4(3):251-256): UTI-Fc3Ser, UTI S10A-Fc3Ser, UTI K21S K22S-Fc3Ser, UTI m2-Fc3Ser, UTI L1-Fc3Ser, UTI L2-Fc3Ser (FIG. 4A). SLIC-based DNA assembly was done by mixing the linearized vector (30 ng), UTI (100 ng) and Fc3Ser (100 ng) PCR products with appropriate overhang sequences for homologous recombination, and T4 DNA polymerase (0.5 U) in 5 μL volume containing NEBuffer 2 and BSA (New England Biolabs). After 30 min incubation at room temperature, the exonuclease activity of T4 DNA polymerase was quenched by adding 2 mM of dCTP. Then in vitro homologous recombination was done by temperature gradient from 75 C. to 37 C. over 30 min. The reaction mixture containing assembled DNA was chemically transformed into TOP10 *E. coli* (Invitrogen), and plated on LB-agar containing carbenicillin. The open reading frames for the remaining constructs (UTI m1-Fc3Ser, UTI d1-Fc3Ser, UTI d2-Fc3Ser, UTI L3-Fc3Ser, UTI-Fc IgG2, Fc3Ser-UTI, and mouse UTI-mouse IgG1) were codon optimized and synthesized as fusion constructs. These constructs were cloned into the expression vector using SLIC method as described above (FIG. 4B). The DNA sequences of all the 13 constructs in the vector were verified by Sanger DNA sequencing.

Example 3

Expression of UTI-Fc Fusions in CHO Cells.

A DNA vector encoding UTI-Fc1 was stably transfected into CHO-S cells using Invitrogen's Freestyle MAX Reagent. Bulk cultures were plated into T-flasks and selected using CD CHO supplemented with various concentrations of methionine sulfoximine (MSX) ranging from 50-100 μM. Once the cultures recovered from selection, they were expanded for production and cryopreservation. Multiple production batches were done to support in vitro and in vivo testing. The production process is a 10-14 day fed-batch culture using CD FortiCHO, CD Efficient Feed B, and CD Efficient Feed C from Invitrogen. The production volumes ranged from 1 L-3 L, and the cultures were harvested by centrifugation at 3500 rpm for 1-2 hours followed by sterile filtration of the supernatant and the resulting cell supernatant was used in purification.

Example 4

Purification of UTI-Fc Fusion Proteins.

Purification of 2 batches of UTI-Fc1 was done by appling 2.3 liters CHO cell conditioned media with expressed UTI-Fc1 to 30 ml protein A mAb select 1× (GE healthcare) equilibrated in 25 mM trisodium citrate pH 8.1, 125 mM NaCl. The column was washed with 2 column volumes (60 ml) 25 mM trisodium citrate pH 8.1, 125 mM NaCl and then with 2 column volumes (60 ml) 25 mM trisodium citrate pH 8.1, 2000 mM NaCl. The column was then equilibrated with 2 column volumes (60 ml) 25 mM trisodium citrate pH 8.1, 125 mM NaCl. UTI-Fc1 was eluted with a 7 column volume (210 ml) gradient to 100% 25 mM citric acid pH 2.9, 125 mM NaCl. The UTI-Fc1 eluted as two peaks, a broad, flanking peak at an approximate pH of 5.5 and a sharper peak at an approximate pH of 3.5. Then, the concentrated UTI-Fc was buffer exchanged into a final buffer of TBS pH 7.4 (25 mM tris, 130 mM NaCl, 2.7 mM KCl pH 7.4) using Amicon Ultra centrifugal concentrators with a 30 K M.W.C.O. Purified protein yields are shown in TABLE 1 and the protein was stored at −80° C. for further use.

TABLE 1

| Peak name | Peak volume (mL) | Final product conc. (mg/mL) | Final product Yield (mg) | Protein A Column Yield (%) | % of total protein load |
|---|---|---|---|---|---|
| 1st batch peak | 40 | 10 | 110 | 59 | 52 |
| 2nd batch peak | 40 | 11 | 150 | 72 | 68 |

Example 5

Expression and Purification of Additional UTI-Fc Fusion Proteins.

On the day of transfection, CHO cells were counted and seeded at density of 2.2×10^6 live cells/mL in 90% of total volume—900 mLs and grown in shaker flasks at 33° C. until transfection. Frozen DNA was thawed and added to PEI (Polyethylenimine—a cationic polymer) and AKT. DNA was added at 0.625 ug/1 million cells. 1 L of cells requires 1.25 mg. 90% of the total DNA added is DNA of interest=1.125 mgs. The remaining 10% was AKT (encodes anti-apoptotic protein)=0.125 mgs. PEI was added at 2.5 ug/1 million cells. For a 1 L transfection this was 5 mg. The PEI solution was added to the diluted DNA and incubated at room temperature for 15 minutes before addition of the DNA complex to the cells.

Cultures were grown at 33° C., 5% CO2, and 125 rpm. 1 to 4 hours post-transfection, 0.6 mM Valproic acid was added. For the 1 L transfection, this was 2 mL of 300 mM stock. On day 1, 1:250 anti-clumping agent was added i.e. 4 mLs/1 L and 15% v/v CD Efficient Feed C i.e. 150 mLs/1 L. On Day 5 and Day 9 15% CD Efficient Feed C was added.

Cells supernatents were harvested on Day 14, cells were counted and protein titers were determined. Cells were spun down by centrifugation at 3000 rpm for 30 minutes at 4° C. The supernatants were filtered through a 0.2 micron filter and stored at 4° C. or frozen at −20° C.

Purification of UTI-Fc fusions was done by Protein A chromatography. 200 mL of cell culture supernant was mixed with 2 ml of MabSelect Sure Protein A Sepharose beads and shaken overnight at 4° C. The bead mixture was then centrifuged in 50 ml tubes at 1200 rpm for 5 minutes and the supernatant was discarded. The beads are added to a column and washed thrice with binding buffer (Biorad, Hercules, Calif.). UTI-fusions were eluted with 8 ml MAPS II Elution buffer (Biorad, Hercules, Calif.). 2 ml of neutralization solution (1 M Tris-HCl pH 8) was added. Samples were then buffer exchanged into 25 mM Citrate, 125 mM NaCl, pH 5.5 by repeated concentration and dilution with the buffer using Amicon Centrifugal units (30 MWCO, 15 mLs, Millipore). FIG. 9 lists the purifications results of various UTI fusion proteins.

Example 6

Inhibition of Proteases by UTI Fusion Proteins

In vitro enzymatic Assay for Trypsin Inhibition by UTI-Fc fusion protein

Solutions of UTI-Fc1 at various concentrations 200 nM final concentration) are prepared in 50 mM HEPES, 150 mM NaCl, 20 mM CaCl2 and 0.01% Brij L23, pH 7.4. Activity assays were performed in Greiner 384-well small volume plates. All steps were conducted at ambient temperature.

Human pancreatic trypsin (1.5 nM final concentration) (Athens Research & Technology, Inc) was added to the dilutions then pre-incubated with the test UTI-Fc for 15 minutes. Next, the reaction was initiated with 100 μM (final) of substrate N☐-Benzoyl-L-arginine-7-amido-4-methylcoumarin hydrochloride SIGMA B7260-25 MG. The reaction mixture total volume was 20 ☐l. Trypsin activity was determined via fluorescence. For example, the fluorescence intensity was determined in kinetic mode over a window of 30 to 60 minutes on a BMG PHERAstar FS or PHERAstar plus using an excitation wavelength of 370 nm and an emission wavelength of 470 nm. Trypsin activity was linearly proportional to the change in fluorescence observed (final−initial). The percent inhibition of Trypsin at a given UTI-Fc concentration was defined as:

Percent inhibition=100*(1−((Fi−Fp)/(Fn−Fp)))

Where: Fi was the observed fluorescence at a given concentration of test UTI-Fc.

Fp was the observed fluorescence of a positive control i.e., the average value of 2 to 6 assays in the absence of Trypsin.

Fn was the observed fluorescence of a negative control i.e., the average value of 2 to 6 assays of Trypsin in the presence of vehicle alone.

Figure 5:
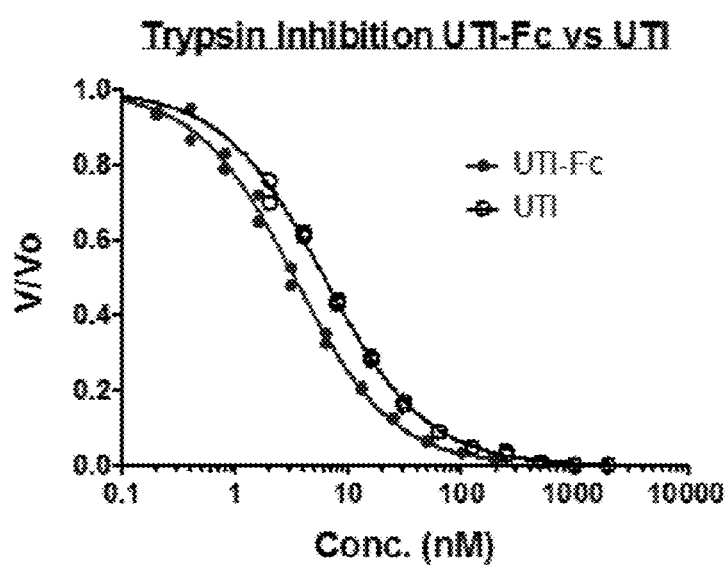
FIG. 5 Supression of protease activity (trypsin) by UTI and UTI-Fc1, SEQ ID NO:1

The IC50 (the molar concentration of the compound, i.e., fusion protein, that produces 50% inhibition) of a test compound, i.e., fusion protein, was calculated by non-linear least squares curve fitting of the equation Percent inhibition=Bottom+((Top-Bottom)/(1+((IC50/[UTI-Fc])^Hill))). Included within the panel of UTI-Fc was one positive control. As shown in FIG. 5, humanUTI has an IC50 of ~3 nM.

Figure 6:
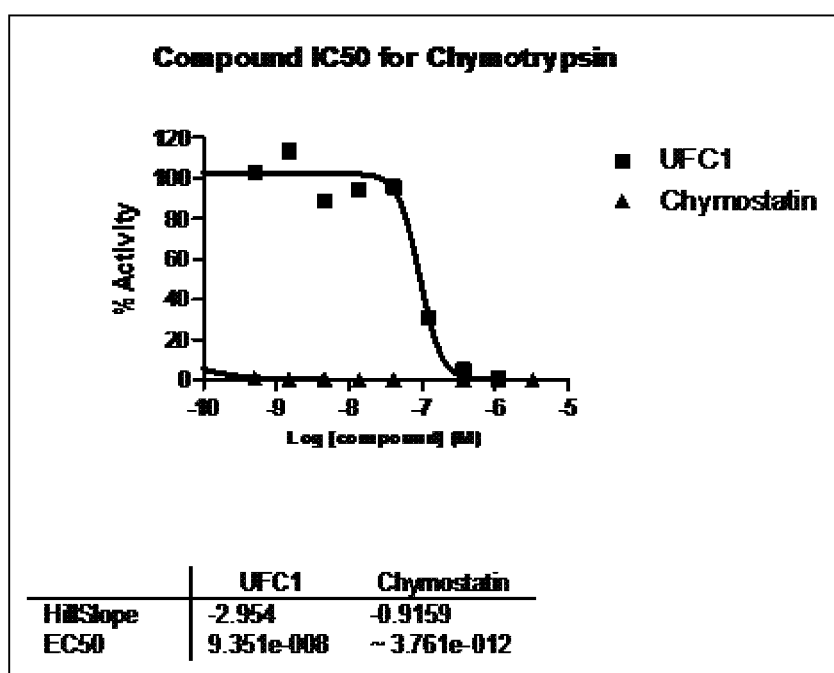
FIG. 6 Supression of protease activity (chymotrypsin) by UTI-Fc1, UFC1, SEQ ID NO:1.

Measurement of the inhibition of other proteases by UTI-Fc1 was also measured at Reaction Biology Corporation (Malvern, Pa.). FIG. 6 demonstrates UTI-Fc1's inhibition of chymotrypsin. FIG. 7 lists the inhibitory constants of UTI-Fc1 for a variety of proteases. UTI-Fc1 inhibits chymotrypsin and plasmin moderately and shows weak inhibition of caspase-1, cathepsin C, and papain.

Example 7

Cellular Effects of Treatment with UTI Fusion Proteins

UTI-Fc1 inhibition of cytokine release was measure in a cell-based assay. BEAS2B cells were seeded at the density of 20,000 cells/well in 96 well plate and cultured using complete BEGM Bullet Kit (Lonza) in CO2 incubator. After 24 hours, the culture media were replaced with plain DMEM for starvation and cells were cultured overnight. Then cells were incubated with fresh plain DMEM containing 100 nM trypsin with various concentrations of human urine UTI or recombinant UTI-Fc1 proteins. After 8 hours, culture supernatants were collected and IL-6 protein levels were assessed using human IL-6 DuoSet (R&D Systems).

Figure 8:
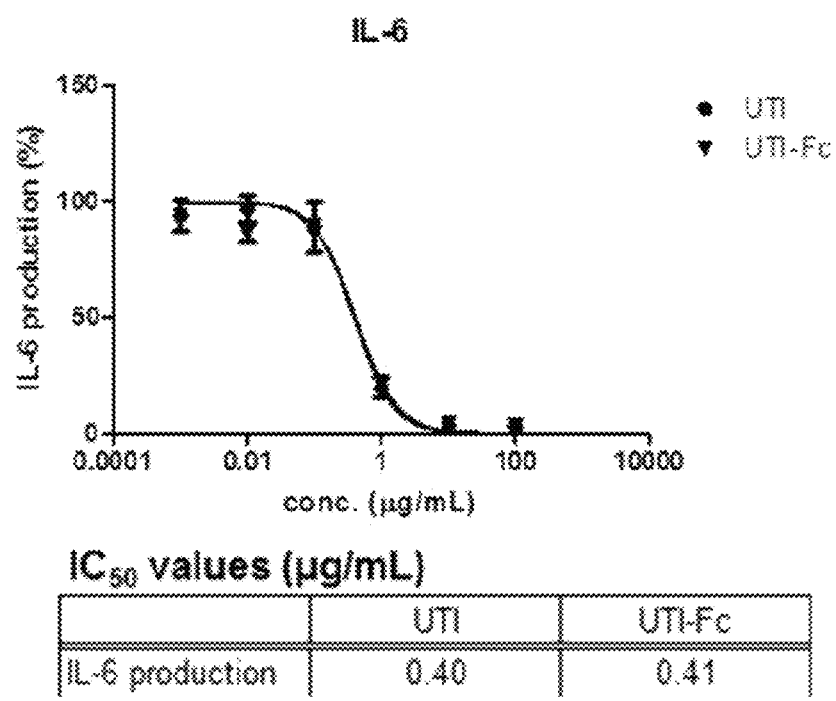
FIG. 8 Supression of cytokine secreation (IL-6) by UTI and UTI-Fc1, UTI-Fc, SEQ ID NO:1.

The results demonstrate that both UTI and UTI-Fc decreased trypsin-induced IL-6 production in BEAS2B cells. As shown in FIG. 8, inhibition was dose-dependent with the IC50 values of 0.40 and 0.41 μg/mL, respectively.

Example 8

Stability Measurements of UTI-Fc Molecules—Thermal Denaturation

Assays were performed to measure the thermal and real-time stability. All molecules demonstrated activity in trypsin inhibition. Thermal stability was measured by differential scanning calorimetry on a Microcal VP-DSC calorimeter. Samples were prepared at 1 mg/ml and buffered in 0.25 mM Tris pH7.4, 0.13M NaCl and 0.0027M KCl. Samples were heated from 25° C. to 110° C. at a rate of 200° C. per hour. UTI-Fc1 was compared to Application Publication Number CN 103044554 A, SEQ ID's 2 and 6, which comprise an IgG2 or IgG1 Fc domain respectively. The results are presented in Table 8.

TABLE 8

| Protein | DSC Tm1 (° C.) | DSC Tm2 (° C.) |
|---|---|---|
| UTI-Fc1 (SEQ ID NO: 1) | 70.86 | 85.79 |
| CN 103044554 A SEQ ID 6 | 68.72 | 86.38 |
| CN 103044554 A SEQ ID 2 | 68.47 | 79.22 |

Example 9

Real-Time Stability Measurements

Real-time stability measurements were performed by incubating SEQ ID NO:1 (UTI-Fc1) or CN 103044554 A, SEQ IDS 2 or 6 at 2-8° C., and 40° C. for 0, 2 and 4 weeks in TBS, pH7.4 buffer. The formation of higher and lower molecular weight species was determined by size exclusion chromatography (SEC) and visualized with polyacrilamide gel electrophoresis (PAGE). The concentration of each UTI-Fc was also monitored by determination of the absorbance of the solution at 280 nm (A280), using extinction coefficients determine by the protein composition. The UTI-Fc molecules produce two, partially overlapping peaks, when analyzed by SEC. The percentage peak area in each UTI-Fc sample measured by SEC is reported in Table 9 at time=0 weeks, 2 weeks, and 4 weeks. Also shown is the percentage change in concentration measured by A280 (% Δ (mg/ml)) at time=2 weeks and 4 weeks. The initial T0 concentration of each sample was UTI-Fc1=33.5 mg/mL, CN 103044554 A SEQ ID 2=8.5 mg/mL, and CN 103044554 A SEQ ID 6=5.6 mg/mL. A variability of 3% is typical for SEC and 15% for individual UV measurements. Analysis by PAGE showed that each UTI-Fc molecule showed the expected banding pattern for full-length UTI-Fc.

TABLE 9

| Protein | SEC 0 weeks | SEC 2 weeks | SEC 4 weeks | % Δ (mg/ml) 2 weeks | % Δ (mg/ml) 4 weeks |
|---|---|---|---|---|---|
| UTI-Fc1 (SEQ ID NO: 1) | Peak1 35.7% Peak2 64.3% | NA | NA | NA | NA |
| UTI-Fc1 (SEQ ID NO: 1) at 2-8° C. | NA | Peak1 36.2% Peak2 63.8% | Peak1 36.1% Peak2 63.9% | 9.2% | 1.2% |
| UTI-Fc1 (SEQ ID NO: 1) at 40° C. | NA | Peak1 37.1% Peak2 62.9% | Peak1 36.8% Peak2 63.2% | 0.2% | 11.9% |
| CN 103044554 A SEQ ID 2 | Peak1 30.6% Peak2 69.4% | NA | NA | NA | NA |
| CN 103044554 A SEQ ID 2 at 2-8° C. | NA | Peak1 29.0% Peak2 71.0% | Peak1 31.5% Peak2 68.5% | 0.2% | 2.7% |
| CN 103044554 A SEQ ID 2 at 40° C. | NA | Peak1 28.2% Peak2 71.8% | Peak1 30.3% Peak2 69.7% | 1.6% | 3.5% |

TABLE 9-continued

| Protein | SEC 0 weeks | SEC 2 weeks | SEC 4 weeks | % Δ (mg/ml) 2 weeks | % Δ (mg/ml) 4 weeks |
|---|---|---|---|---|---|
| CN 103044554 A SEQ ID 6 | Peak 1 36.6% Peak 2 63.4% | NA | NA | NA | NA |
| CN 103044554 A SEQ ID 6 at 2-8° C. | NA | Peak1 34.8% Peak2 65.2% | Peak1 36.4% Peak2 63.6% | 7.8% | 9.5% |
| CN 103044554 A SEQ ID 6 at 40° C. | NA | Peak1 33.9% Peak2 66.1% | Peak1 34.5% Peak2 65.5% | 3.6% | 6.0% |

Example 10

In vivo Tests of Complement Inhibition

Figure 10:
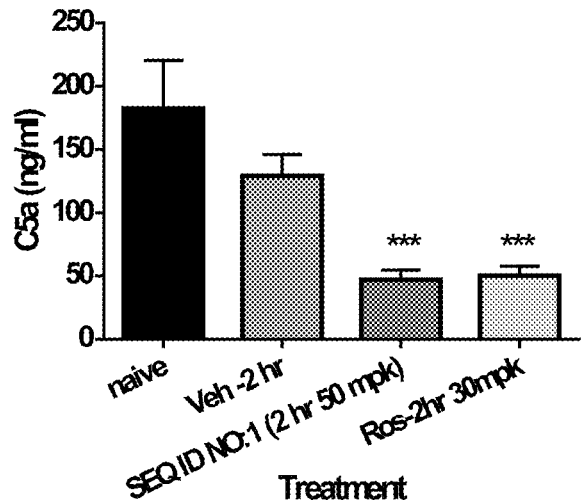
FIG. 10 Effect of SEQ ID NO:1 on LPS Induced C5a in C3H Mice.
Figure 10:
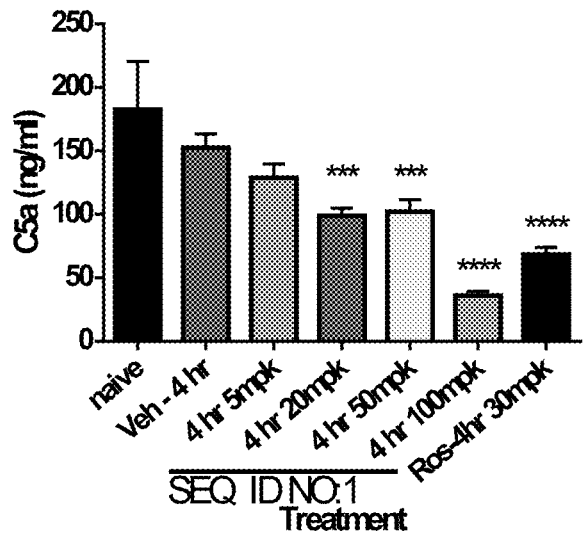

UTI-Fc1 (SEQ ID NO:1) affects on the complement system were measured in vivo. Female, C3h/HeJ mice were purchased from Jackson Laboratories. Animals are dosed according to the experimental design Table 10. Animals were injected i.p. (100 ul/mouse) 15 minutes post dose with LPS at time zero. Animals were euthanized at 2 and 4 hours post LPS injection by CO2 overdose and blood was collected by cardiac puncture. Blood was transferred to serum separator microtubes and allowed to clot at room temperature for 30 minutes. Subsequently, microtubes were centrifuged at 12,000 rpm for 5 minutes and serum was removed and aliquoted to a 96 well plate. Rosmarinic acid was used as a positive control and used as 3 mg/ml in saline. The 96 well plate was frozen at −20° C. Serum samples were analyzed for C5a content by duoset. Statistical significance was determined using Prism graphing software and effects were considering statistically significant if p<0.05. As shown in FIG. 10, SEQ ID NO:1 (UTI-Fc1) significantly reduced C5a at 20, 50, and 100 mg/kg at 4 hours post LPS dose.

TABLE 10

Experimental Design (UTI-Fc1 is SEQ ID: 1)

| Group | Description | Dose (mg/kg) | Conc. (mg/ml) | Volume (ml/kg) | Route | Stimulation LPS (i.p) | LPS conc. (mg/ml) | Animals |
|---|---|---|---|---|---|---|---|---|
| 1 | naive | — | — | — | — | — | — | 8 |
| 2 | Veh -2 hr | — | — | 10 | iv | 30 ug | 0.3 | 8 |
| 3 | UTI-Fc1 -2 hr | 50 | 5.0 | 10 | iv | 30 ug | 0.3 | 8 |
| 4 | Ros_2 hr_30mpk | 30 | 3.0 | 10 | sc | 30 ug | 0.3 | 8 |
| 5 | Veh - 4 hr | — | — | 10 | iv | 30 ug | 0.3 | 8 |
| 6 | UTI-Fc1 -4 hr_5mpk | 5 | 0.5 | 10 | iv | 30 ug | 0.3 | 8 |
| 7 | UTI-Fc1 -4 hr_20mpk | 20 | 2.0 | 10 | iv | 30 ug | 0.3 | 8 |
| 8 | UTI-Fc1 -4 hr_50mpk | 50 | 5.0 | 10 | iv | 30 ug | 0.3 | 8 |
| 9 | UTI-Fc1 -4 hr_100mpk | 100 | 10.0 | 10 | iv | 30 ug | 0.3 | 8 |
| 10 | Ros_4 hr_30mpk | 30 | 3.0 | 10 | sc | 30 ug | 0.3 | 8 |

```
SEQUENCE LISTING
UTI-Fc 1 Protein Sequence                                              SEQ ID NO: 1

AVLPQEEEGSGGGQLVTEVTKKEDSCQLGYSAGPCMGMTSRYFYNGTSMACETFQ

YGGCMGNGNNFVTEKECLQTCRTVAACNLPIVRGPCRAFIQLWAFDAVKGKCVLFP

YGGCQGNGNKFYSEKECREYCGVPGDGDEELLGSGGGGDKTHTCPPCPAPELLGGP

SVFLFPPKPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQPREPQVYT

LPPSREEMTKNQVSLTCLVKGFYPSDIAVEWESNGQPENNYKTTPPVLDSDGSFFLYS

KLTVDKSRWQQGNVFSCSVMHEALHNHYTQKSLSLSPG

UTI-Fc 1 DNA Sequence                                                 SEQ ID NO: 2

GCTGTGCTGCCTCAGGAAGAGGAAGGCTCTGGCGGAGGCCAGCTCGTGACCGAA

GTGACCAAGAAAGAGGACTCCTGCCAGCTGGGCTACTCTGCCGGCCCTTGTATGG

GCATGACCTCCCGGTACTTCTACAACGGCACCTCCATGGCCTGCGAGACATTCCA

GTACGGCGGCTGCATGGGCAACGGCAACAACTTTGTGACAGAGAAAGAGTGCCT

GCAGACCTGCAGAACCGTGGCCGCCTGTAACCTGCCTATCGTGCGGGGACCCTGT

CGGGCCTTTATCCAGCTGTGGGCCTTCGACGCCGTGAAGGGCAAATGCGTGCTGT

TCCCCTATGGCGGCTGCCAGGGAAATGGAAACAAGTTCTACTCCGAGAAAGAAT
```

```
GCCGCGAGTACTGTGGCGTGCCAGGCGACGGGGATGAGGAACTGCTGGGATCAG

GCGGCGGAGGCGACAAGACCCATACCTGTCCACCTTGCCCTGCCCCCGAGCTGCT

GGGAGGACCTTCTGTGTTCCTGTTCCCCCCAAAGCCCAAGGACACCCTGATGATC

TCCCGGACCCCTGAAGTGACCTGCGTGGTGGTGGATGTGTCCCACGAGGATCCCG

AAGTGAAGTTCAATTGGTACGTGGACGGCGTGGAAGTGCACAACGCCAAGACCA

AGCCCAGAGAGGAACAGTACAACTCCACCTACCGGGTGGTGTCCGTGCTGACCG

TGCTGCACCAGGATTGGCTGAACGGCAAAGAGTACAAGTGCAAGGTGTCCAACA

AGGCCCTGCCTGCCCCCATCGAAAAGACCATCTCCAAGGCCAAGGGCCAGCCCC

GGGAACCCCAGGTGTACACACTGCCCCCTAGCCGGGAAGAGATGACAAAGAACC

AGGTGTCCCTGACCTGTCTCGTGAAGGGATTCTACCCCTCCGATATCGCCGTGGA

ATGGGAGTCCAACGGCCAGCCTGAGAACAACTACAAGACCACCCCCCCTGTGCT

GGACTCCGACGGCTCATTCTTCCTGTACTCCAAGCTGACAGTGGACAAGTCCCGG

TGGCAGCAGGGCAACGTGTTCTCCTGCTCCGTGATGCACGAGGCCCTGCACAACC

ACTACACCCAGAAGTCCCTGTCCCTGAGCCCCGGC
```

UTI-Fc IgG1 3Ser Protein sequence
SEQ ID NO: 3 avlpqeeegsgggqlvtevtkkedscqlgysagpcmgmtsryfyngtsmacetfqyggcmgngnnfvtekeclqtcrtvaacn lpivrgpcrafiqlwafdavkgkcvlfpyggcqgngnkfysekecreycgvpgdgdeellrepkssdkthtcppcpapellggss vflfppkpkdtlmisrtpevtcvvvdvshedpevkfnwyvdgvevhnaktkpreeqynstyrvvsvltvlhqdwlngkeykck vsnkalpasiektiskakgqprepqvytlppsreemtknqvsltclvkgfypsdiavewesngqpennykttppvldsdgsfflys kltvdksrwqqgnvfscsvmhealhnhytqkslslspg UTI-Fc IgG1 3Ser DNA sequence
SEQ ID NO: 4 gctgtgctgcctcaggaagaggaaggctctggcggaggccagctcgtgaccgaagtgaccaagaaagaggactcctgccagctgg gctactctgccggcccttgtatgggcatgacctcccggtacttctacaacggcacctccatggcctgcgagacattccagtacggcgg ctgcatgggcaacggcaacaactttgtgacagagaaagagtgcctgcagacctgcagaaccgtggccgcctgtaacctgcctatcgt gcggggaccctgtcgggcctttatccagctgtgggccttcgacgccgtgaagggcaaatgcgtgctgttccctatggcggctgcca gggaaatggaaacaagttctactccgagaaagaatgccgcgagtactgtggcgtgccaggcgacggggatgaggaactgctgcgg gagcccaaatcttccgacaagacccatacctgtccaccttgccctgcccccgagctgctgggaggatcctctgtgttcctgttcccccc aaagcccaaggacaccctgatgatctcccggacccctgaagtgacctgcgtggtggtggatgtgtcccacgaggatcccgaagtgaa gttcaattggtacgtggacggcgtggaagtgcacaacgccaagaccaagcccagagaggaacagtacaactccacctaccgggtg gtgtccgtgctgaccgtgctgcaccaggattggctgaacggcaaagagtacaagtgcaaggtgtccaacaaggccctgcctgcctcc atcgaaaagaccatctccaaggccaagggccagccccgggaaccccaggtgtacacactgccccctagccgggaagagatgaca aagaaccaggtgtccctgacctgtctcgtgaagggattctacccctccgatatcgccgtggaatgggagtccaacggccagcctgag aacaactacaagaccaccccccctgtgctggactccgacggctcattcttcctgtactccaagctgacagtggacaagtcccggtggc agcagggcaacgtgttctcctgctccgtgatgcacgaggccctgcacaaccactacacccagaagtccctgtccctgagccccggc UTI-Fc IgG2 Ser Protein sequence
SEQ ID NO: 5 avlpqeeegsgggqlvtevtkkedscqlgysagpcmgmtsryfyngtsmacetfqyggcmgngnnfvtekeclqtcrtvaacn lpivrgperafiqlwafdavkgkcvlfpyggcqgngnkfysekecreycgvpgdgdeellrkscvecppcpappvagpsvflfp pkpkdtlmisrtpevtcvvvdvshedpevqfnwyvdgmevhnaktkpreeqfnstfrvvsvltvvhqdwlngkeykckvsn kglpapiektisktkgqprepqvytlppsreemtknqvsltclvkgfypsdiavewesngqpennykttppmldsdgsfflysklt vdksrwqqgnvfscsvmhealhnhytqkslslspgk UTI-Fc IgG2 Ser DNA sequence

SEQ ID NO: 6 gctgtgctgcctcaggaagaggaaggctctggcggaggccagctcgtgaccgaagtgaccaagaaagaggactcctgccagctgg
gctactctgccggcccttgtatgggcatgacctcccggtacttctacaacggcacctccatggcctgcgagacattccagtacggcgg
ctgcatgggcaacggcaacaactttgtgacagagaaagagtgcctgcagacctgcagaaccgtggccgcctgtaacctgcctatcgt
gcggggaccctgtcgggcctttatccagctgtgggccttcgacgccgtgaagggcaaatgcgtgctgttccctatggcggctgcca
gggaaatggaaacaagttctactccgagaaagaatgccgcgagtactgtggcgtgccaggcgacggggatgaggaactgctgcgg
aaatcctgtgtcgagtgcccaccgtgcccagcaccacctgtggcaggaccgtcagtcttcctcttcccccaaaacccaaggacaccc
tcatgatctcccggaccccgaggtcacgtgcgtggtggtggacgtgagccacgaagaccccgaggtccagttcaactggtacgtgg
acggcatggaggtgcataatgccaagacaaagccacgggaggagcagttcaacagcacgttccgtgtggtcagcgtcctcaccgtc
gtgcaccaggactggctgaacggcaaggagtacaagtgcaaggtctccaacaaaggcctcccagcccccatcgagaaaaccatctc
caaaaccaaagggcagccccgagaaccacaggtgtacaccctgcccccatcccgggaggagatgaccaagaaccaggtcagcct
gacctgcctggtcaaaggcttctaccccagcgacatcgccgtggagtgggagagcaatgggcagccggagaacaactacaagacc
acacctcccatgctggactccgacggctccttcttcctctacagcaagctcaccgtggacaagagcaggtggcagcaggggaacgtc
ttctcatgctccgtgatgcatgaggctctgcacaaccactacacacagaagagcctctccctgtctccgggtaaa UTI-Fc IgG2 Protein sequence

SEQ ID NO: 7 avlpqeeegsgggqlvtevtkkedscqlgysagpcmgmtsryfyngtsmacetfqyggcmgngnnfvtekeclqtcrtvaacn
lpivrgperafiqlwafdavkgkcvlfpyggcqgngnkfysekecreycgvpgdgdeellrkccvecppcpappvagpsvflfp
pkpkdtlmisrtpevtcvvvdvshedpevqfnwyvdgmevhnaktkpreeqfnstfrvvsvltvvhqdwlngkeykckvsn
kglpapiektisktkgqprepqvytlppsreemtknqvsltclvkgfypsdiavewesngqpennykttppmldsdgsfflysklt
vdksrwqqgnvfscsvmhealhnhytqkslslspgk UTI-Fc IgG2 DNA sequence

SEQ ID NO: 8 gctgtgctgcctcaggaagaggaaggctctggcggaggccagctcgtgaccgaagtgaccaagaaagaggactcctgccagctgg
gctactctgccggcccttgtatgggcatgacctcccggtacttctacaacggcacctccatggcctgcgagacattccagtacggcgg
ctgcatgggcaacggcaacaactttgtgacagagaaagagtgcctgcagacctgcagaaccgtggccgcctgtaacctgcctatcgt
gcggggaccctgtcgggcctttatccagctgtgggccttcgacgccgtgaagggcaaatgcgtgctgttccctatggcggctgcca
gggaaatggaaacaagttctactccgagaaagaatgccgcgagtactgtggcgtgccaggcgacggggatgaggaactgctgcgg
aaatgttgtgtcgagtgcccaccgtgcccagcaccacctgtggcaggaccgtcagtcttcctcttcccccaaaacccaaggacaccc
tcatgatctcccggaccccgaggtcacgtgcgtggtggtggacgtgagccacgaagaccccgaggtccagttcaactggtacgtgg
acggcatggaggtgcataatgccaagacaaagccacgggaggagcagttcaacagcacgttccgtgtggtcagcgtcctcaccgtc
gtgcaccaggactggctgaacggcaaggagtacaagtgcaaggtctccaacaaaggcctcccagcccccatcgagaaaaccatctc
caaaaccaaagggcagccccgagaaccacaggtgtacaccctgcccccatcccgggaggagatgaccaagaaccaggtcagcct
gacctgcctggtcaaaggcttctaccccagcgacatcgccgtggagtgggagagcaatgggcagccggagaacaactacaagacc
acacctcccatgctggactccgacggctccttcttcctctacagcaagctcaccgtggacaagagcaggtggcagcaggggaacgtc
ttctcatgctccgtgatgcatgaggctctgcacaaccactacacacagaagagcctctccctgtctccgggtaaa UTI-Fc IgG1 3Ser S10A Protein sequence

SEQ ID NO: 9 avlpqeeegagggqlvtevtkkedscqlgysagpcmgmtsryfyngtsmacetfqyggcmgngnnfvtekeclqtcrtvaacn
lpivrgperafiqlwafdavkgkcvlfpyggcqgngnkfysekecreycgvpgdgdeellrepkssdkthtcppcpapellggss
vflfppkpkdtlmisrtpevtcvvvdvshedpevkfnwyvdgvevhnaktkpreeqynstyrvvsvltvlhqdwlngkeykck
vsnkalpasiektiskakgqprepqvytlppsreemtknqvsltclvkgfypsdiavewesngqpennykttppvldsdgsfflys
kltvdksrwqqgnvfscsvmhealhnhytqkslslspg UTI-Fc IgG1 3Ser S10A DNA sequence

SEQ ID NO: 10 gctgtgctgcctcaggaagaggaaggcgcaggcggaggccagctcgtgaccgaagtgaccaagaaagaggactcctgccagctg
ggctactctgccggccttgtatgggcatgacctcccggtacttctacaacggcacctccatggcctgcgagacattccagtacggcg
gctgcatgggcaacggcaacaactttgtgacagagaaagagtgcctgcagacctgcagaaccgtggccgcctgtaacctgcctatcg
tgcggggaccctgtcgggcctttatccagctgtgggccttcgacgccgtgaagggcaaatgcgtgctgttcccctatggcggctgcca
gggaaatggaaacaagttctactccgagaaagaatgccgcgagtactgtggcgtgccaggcgacggggatgaggaactgctgcgg
gagcccaaatcttccgacaagacccatacctgtccaccttgccctgcccccgagctgctgggaggatcctctgtgttcctgttccccc
aaagcccaaggacaccctgatgatctcccggacccctgaagtgacctgcgtggtggtggatgtgtcccacgaggatcccgaagtgaa
gttcaattggtacgtggacggcgtggaagtgcacaacgccaagaccaagcccagagaggaacagtacaactccacctaccgggtg
gtgtccgtgctgaccgtgctgcaccaggattggctgaacggcaaagagtacaagtgcaaggtgtccaacaaggccctgcctgcctcc
atcgaaaagaccatctccaaggccaagggccagccccgggaaccccaggtgtacacactgcccctagccgggaagagatgaca
aagaaccaggtgtccctgacctgtctcgtgaagggattctacccctccgatatcgccgtggaatgggagtccaacggccagcctgag
aacaactacaagaccacccccctgtgctggactccgacggctcattcttcctgtactccaagctgacagtggacaagtcccggtggc
agcagggcaacgtgttctcctgctccgtgatgcacgaggccctgcacaaccactacacccagaagtccctgtccctgagccccggc UTI-Fc IgG1 3Ser m2 Protein sequence

SEQ ID NO: 11 edscqlgysagpcmgmtsryfyngtsmacetfqyggcmgngnnfvtekeclqtcrtvaacnlpivrgpcrafiqlwafdavkg
kcvlfpyggcqgngnkfysekecreycgvpgdgdeellrepkssdkthtcppcpapellggssvflfppkpkdtlmisrtpevtc
vvvdvshedpevkfnwyvdgvevhnaktkpreeqynstyrvvsvltvlhqdwingkeykckvsnkalpasiektiskakgqp
repqvytlppsreemtknqvsltclvkgfypsdiavewesngqpennyktppvldsdgsfflyskltvdksrwqqgnvfscsv
mhealhnhytqkslslspg UTI-Fc IgG1 3Ser m2 DNA sequence

SEQ ID NO: 12 gaggactcctgccagctgggctactctgccggccttgtatgggcatgacctcccggtacttctacaacggcacctccatggcctgcg
agacattccagtacggcggctgcatgggcaacggcaacaactttgtgacagagaaagagtgcctgcagacctgcagaaccgtggcc
gcctgtaacctgcctatcgtgcggggaccctgtcgggcctttatccagctgtgggccttcgacgccgtgaagggcaaatgcgtgctgtt
cccctatggcggctgccagggaaatggaaacaagttctactccgagaaagaatgccgcgagtactgtggcgtgccaggcgacggg
gatgaggaactgctgcgggagcccaaatcttccgacaagacccatacctgtccaccttgccctgcccccgagctgctgggaggatcc
tctgtgttcctgttccccccaaagcccaaggacaccctgatgatctcccggacccctgaagtgacctgcgtggtggtggatgtgtccca
cgaggatcccgaagtgaagttcaattggtacgtggacggcgtggaagtgcacaacgccaagaccaagcccagagaggaacagtac
aactccacctaccgggtggtgtccgtgctgaccgtgctgcaccaggattggctgaacggcaaagagtacaagtgcaaggtgtccaac
aaggccctgcctgcctccatcgaaaagaccatctccaaggccaagggccagccccgggaaccccaggtgtacacactgccccta
gccgggaagagatgacaaagaaccaggtgtccctgacctgtctcgtgaagggattctacccctccgatatcgccgtggaatgggagt
ccaacggccagcctgagaacaactacaagaccacccccctgtgctggactccgacggctcattcttcctgtactccaagctgacagt
ggacaagtcccggtggcagcagggcaacgtgttctcctgctccgtgatgcacgaggccctgcacaaccactacacccagaagtccct
gtccctgagccccggc UTI-Fc IgG1 3Ser m1 Protein sequence

SEQ ID NO: 13 avlpqeeegsggggqlvtevtkkepkssdkthtcppcpapellggssvflfppkpkdtlmisrtpevtcvvvdvshedpevkfnw
yvdgvevhnaktkpreeqynstyrvvsvltvlhqdwlngkeykckvsnkalpasiektiskakgqprepqvytlppsreemtkn
qvsltclvkgfypsdiavewesngqpennyktppvldsdgsfflyskltvdksrwqqgnvfscsvmhealhnhytqkslslspg UTI-Fc IgG1 3Ser m1 DNA sequence
SEQ ID NO: 14 gctgtgctgcctcaggaagaggaaggctctggcggaggccagctcgtgaccgaagtgaccaagaaagagcccaaatcttccgaca agacccatacctgtccaccttgccctgcccccgagctgctgggaggatcctctgtgttcctgttccccccaaagcccaaggacaccctg atgatctcccgaccccctgaagtgacctgcgtggtggtggatgtgtcccacgaggatcccgaagtgaagttcaattggtacgtggacg gcgtggaagtgcacaacgccaagaccaagcccagagaggaacagtacaactccacctacccgggtggtgtccgtgctgaccgtgct gcaccaggattggctgaacggcaaagagtacaagtgcaaggtgtccaacaaggccctgcctgcctccatcgaaaagaccatctcca aggccaagggccagccccgggaaccccaggtgtacacactgcccccctagccgggaagagatgacaaagaaccaggtgtccctga cctgtctcgtgaagggattctaccctccgatatcgccgtggaatgggagtccaacggccagcctgagaacaactacaagaccaccc cccctgtgctggactccgacggctcattcttcctgtactccaagctgacagtggacaagtcccggtggcagcagggcaacgtgttctcc tgctccgtgatgcacgaggccctgcacaaccactacacccagaagtccctgtccctgagccccggc UTI-Fc IgG1 3Ser link3 Protein sequence
SEQ ID NO: 15 avlpqeeegsgggqlvtevtkkedscqlgysagpcmgmtsryfyngtsmacetfqyggcmgngnnfvtekeclqtcrtvaacn lpivrgperafiqlwafdavkgkcvlfpyggcqgngnkfysekecreycgvpgdgdeellggggsggggsepkssdkthtcppc papellggssvflfppkpkdtlmisrtpevtcvvvdvshedpevkfnwyvdgvevhnaktkpreeqynstyrvvsyltvlhqdw lngkeykckvsnkalpasiektiskakgqprepqvytlppsreemtknqvsltclvkgfypsdiavewesngqpennyktttppvl dsdgsfflyskltvdksrwqqgnvfscsvmhealhnhytqkslslspg UTI-Fc IgG1 3Ser link3 DNA sequence
SEQ ID NO: 16 gctgtgctgcctcaggaagaggaaggctctggcggaggccagctcgtgaccgaagtgaccaagaaagaggactcctgccagctgg gctactctgccggcccttgtatgggcatgacctcccggtacttctacaacggcacctccatggcctgcgagacattccagtacggcgg ctgcatgggcaacggcaacaactttgtgacagagaaagagtgcctgcagacctgcagaaccgtggccgcctgtaacctgcctatcgt gcggggaccctgtcgggcctttatccagctgtgggccttcgacgccgtgaagggcaaatgcgtgctgttcccctatggcggctgcca gggaaatggaaacaagttctactccgagaaagaatgccgcgagtactgtggcgtgccaggcgacggggatgaggaactgctggga ggtggtggatcaggtggcggaggatcagagcccaaatcttccgacaagacccataccctgtccaccttgccctgcccccgagctgctg ggaggatcctctgtgttcctgttccccccaaagcccaaggacaccctgatgatctcccggaccccctgaagtgacctgcgtggtggtgg atgtgtcccacgaggatcccgaagtgaagttcaattggtacgtggacggcgtggaagtgcacaacgccaagaccaagcccagagag gaacagtacaactccacctacccgggtggtgtccgtgctgaccgtgctgcaccaggattggctgaacggcaaagagtacaagtgcaag gtgtccaacaaggccctgcctgcctccatcgaaaagaccatctccaaggccaagggccagccccgggaaccccaggtgtacacact gcccccctagccgggaagagatgacaaagaaccaggtgtccctgacctgtctcgtgaagggattctaccctccgatatcgccgtgga atgggagtccaacggccagcctgagaacaactacaagaccacccccctgtgctggactccgacggctcattcttcctgtactccaag ctgacagtggacaagtcccggtggcagcagggcaacgtgttctcctgctccgtgatgcacgaggccctgcacaaccactaccca gaagtccctgtccctgagccccggc UTI-Fc IgG1 3Ser link2 Protein sequence
SEQ ID NO: 17 avlpqeeegsgggqlvtevtkkedscqlgysagpcmgmtsryfyngtsmacetfqyggcmgngnnfvtekeclqtcrtvaacn lpivrgperafiqlwafdavkgkcvlfpyggcqgngnkfysekecreycgvpgdgdeellrcppcpapellggssvflfppkpkd tlmisrtpevtcvvvdvshedpevkfnwyvdgvevhnaktkpreeqynstyrvvsvltvlhqdwlngkeykckvsnkalpasi ektiskakgqprepqvytlppsreemtknqvsltclvkgfypsdiavewesngqpennykttppvldsdgsfflyskltvdksrw qqgnvfscsvmhealhnhytqkslslspg UTI-Fc IgG1 3Ser link2 DNA sequence
SEQ ID NO: 18 gctgtgctgcctcaggaagaggaaggctctggcggaggccagctcgtgaccgaagtgaccaagaaagaggactcctgccagctgg gctactctgccggcccttgtatgggcatgacctcccggtacttctacaacggcacctccatggcctgcgagacattccagtacggcgg -continued ctgcatgggcaacggcaacaactttgtgacagagaaagagtgcctgcagacctgcagaaccgtggccgcctgtaacctgcctatcgt gcggggaccctgtcgggcctttatccagctgtgggccttcgacgccgtgaagggcaaatgcgtgctgttccctatggcggctgcca gggaaatggaaacaagttctactccgagaaagaatgccgcgagtactgtggcgtgccaggcgacggggatgaggaactgctgcgg tgtccaccttgccctgcccccgagctgctgggaggatcctctgtgttcctgttcccccaaagcccaaggacaccctgatgatctcccg gacccctgaagtgacctgcgtggtggtggatgtgtcccacgaggatcccgaagtgaagttcaattggtacgtggacggcgtggaagt gcacaacgccaagaccaagcccagagaggaacagtacaactccacctaccgggtggtgtccgtgctgaccgtgctgcaccaggatt ggctgaacggcaaagagtacaagtgcaaggtgtccaacaaggccctgcctgcctccatcgaaaagaccatctccaaggccaaggg ccagcccccgggaaccccaggtgtacacactgcccccctagccgggaagagatgacaaagaaccaggtgtccctgacctgtctcgtga agggattctacccctccgatatcgccgtggaatgggagtccaacggccagcctgagaacaactacaagaccaccccccctgtgctgg actccgacggctcattcttcctgtactccaagctgacagtggacaagtcccggtggcagcagggcaacgtgttctcctgctccgtgatg cacgaggccctgcacaaccactacacccagaagtccctgtccctgagccccggc UTI-Fc IgG1 3Ser link1 Protein sequence

SEQ ID NO: 19 avlpqeeegsgggqlvtevtkkedscqlgysagpcmgmtsryfyngtsmacetfqyggcmgngnnfvtekeclqtcrtvaacn lpivrgperafiqlwafdavkgkcvlfpyggcqgngnkfysekecreycgvssvflfppkpkdtlmisrtpevtcvvvdvshedp evkfnwyvdgvevhnaktkpreeqynstyrvvsvltvlhqdwlngkeykckvsnkalpasiektiskakgqprepqvytlppsr eemtknqvsltclvkgfypsdiavewesngqpennykttppvldsdgsfflyskltvdksrwqqgnvfscsvmhealhnhytq kslslspg UTI-Fc IgG1 3Ser link1 DNA sequence

SEQ ID NO: 20 gctgtgctgcctcaggaagaggaaggctctggcggaggccagctcgtgaccgaagtgaccaagaaagaggactcctgccagctgg gctactctgccggcccttgtatgggcatgacctcccggtacttctacaacggcacctccatggcctgcgagacattccagtacggcgg ctgcatgggcaacggcaacaactngtgacagagaaagagtgcctgcagacctgcagaaccgtggccgcctgtaacctgcctatcgt gcggggaccctgtcgggcctttatccagctgtgggccttcgacgccgtgaagggcaaatgcgtgctgttccctatggcggctgcca gggaaatggaaacaagttctactccgagaaagaatgccgcgagtactgtggcgtgtcctctgtgttcctgttcccccaaagcccaag gacaccctgatgatctcccggacccctgaagtgacctgcgtggtggtggatgtgtcccacgaggatcccgaagtgaagttcaattggt acgtggacggcgtggaagtgcacaacgccaagaccaagcccagagaggaacagtacaactccacctaccgggtggtgtccgtgct gaccgtgctgcaccaggattggctgaacggcaaagagtacaagtgcaaggtgtccaacaaggccctgcctgcctccatcgaaaaga ccatctccaaggccaagggccagcccccgggaaccccaggtgtacacactgccccctagccgggaagagatgacaaagaaccagg tgtccctgacctgtctcgtgaagggattctacccctccgatatcgccgtggaatgggagtccaacggccagcctgagaacaactacaa gaccaccccccctgtgctggactccgacggctcattcttcctgtactccaagctgacagtggacaagtcccggtggcagcagggcaa cgtgttctcctgctccgtgatgcacgaggccctgcacaaccactacacccagaagtccctgtccctgagccccggc UTI-Fc IgG1 3Ser K21S K22S Protein sequence

SEQ ID NO: 21 avlpqeeegsgggqlvtevtssedscqlgysagpcmgmtsryfyngtsmacetfqyggcmgngnnfvtekeclqtcrtvaacnl pivrgperafiqlwafdavkgkcvlfpyggcqgngnkfysekecreycgvpdgdeellrepkssdkthtcppcpapellggssv flfppkpkdtlmisrtpevtcvvvdvshedpevkfnwyvdgvevhnaktkpreeqynstyrvvsvltvlhqdwlngkeykckv snkalpasiektiskakgqprepqvytlppsreemtknqvsltclvkgfypsdiavewesngqpennykttppvldsdgsfflysk ltvdksrwqqgnvfscsvmhealhnhytqkslslspg UTI-Fc IgG1 3Ser K21S K22S DNA sequence

SEQ ID NO: 22 gctgtgctgcctcaggaagaggaaggctctggcggaggccagctcgtgaccgaagtgacctcctccgaggactcctgccagctggg ctactctgccggcccttgtatgggcatgacctcccggtacttctacaacggcacctccatggcctgcgagacattccagtacggcggct gcatgggcaacggcaacaactngtgacagagaaagagtgcctgcagacctgcagaaccgtggccgcctgtaacctgcctatcgtgc ggggaccctgtcgggcctttatccagctgtgggccttcgacgccgtgaagggcaaatgcgtgctgttccctatggcggctgccagg -continued gaaatggaaacaagnctactccgagaaagaatgccgcgagtactgtggcgtgccaggcgacggggatgaggaactgctgcggga gcccaaatcttccgacaagacccatacctgtccaccttgccctgcccccgagctgctgggaggatcctctgtgttcctgttcccccaaa gcccaaggacaccctgatgatctcccggacccctgaagtgacctgcgtggtggtggatgtgtcccacgaggatcccgaagtgaagtt caattggtacgtggacggcgtggaagtgcacaacgccaagaccaagcccagagaggaacagtacaactccacctaccgggtggtg tccgtgctgaccgtgctgcaccaggattggctgaacggcaaagagtacaagtgcaaggtgtccaacaaggccctgcctgcctccatc gaaaagaccatctccaaggccaagggccagcccgggaaccccaggtgtacacactgcccctagccgggaagagatgacaaag aaccaggtgtccctgacctgtctcgtgaagggattctaccctccgatatcgccgtggaatgggagtccaacggccagcctgagaaca actacaagaccacccccctgtgctggactccgacggctcattcttcctgtactccaagctgacagtggacaagtcccggtggcagca gggcaacgtgactcctgctccgtgatgcacgaggccctgcacaaccactacacccagaagtccctgtccctgagccccggc UTI-Fc IgG1 3Ser d2 Protein sequence

SEQ ID NO: 23 avlpqeeegsgggqlvtevtkktvaacnlpivrgpcrafiqlwafdavkgkcvlfpyggcqgngnkfysekecreycgvpgdgd eellrepkssdkthtcppcpapellggssvflfppkpkdtlmisrtpevtcvvvdvshedpevkfnwyvdgvevhnaktkpreeq ynstyrvvsvltvlhqdwlngkeykckvsnkalpasiektiskakgqprepqvytlppsreemtknqvsltclvkgfypsdiave wesngqpennykttppvldsdgsfflysklvtdksrwqqgnvfscsvmhealhnhytqkslslspg UTI-Fc IgG1 3Ser d2 DNA sequence

SEQ ID NO: 24 gctgtgctgcctcaggaagaggaaggctctggcggaggccagctcgtgaccgaagtgaccaagaaaaccgtggccgcctgtaacc tgcctatcgtgcggggaccctgtcgggcctttatccagctgtgggccttcgacgccgtgaagggcaaatgcgtgctgttccctatggc ggctgccagggaaatggaaacaagttctactccgagaaagaatgccgcgagtactgtggcgtgccaggcgacggggatgaggaac tgctgcgggagcccaaatcttccgacaagacccatacctgtccaccttgccctgcccccgagctgctgggaggatcctctgtgttcctg ttccccccaaagcccaaggacaccctgatgatctcccggacccctgaagtgacctgcgtggtggtggatgtgtcccacgaggatccc gaagtgaagttcaattggtacgtggacggcgtggaagtgcacaacgccaagaccaagcccagagaggaacagtacaactccaccta ccgggtggtgtccgtgctgaccgtgctgcaccaggattggctgaacggcaaagagtacaagtgcaaggtgtccaacaaggccctgc ctgcctccatcgaaaagaccatctccaaggccaagggccagcccgggaaccccaggtgtacacactgcccctagccgggaaga gatgacaaagaaccaggtgtccctgacctgtctcgtgaagggattctaccctccgatatcgccgtggaatgggagtccaacggcca gcctgagaacaactacaagaccaccccccctgtgctggactccgacggctcattcttcctgtactccaagctgacagtggacaagtcc cggtggcagcagggcaacgtgactcctgctccgtgatgcacgaggccctgcacaaccactacacccagaagtccctgtccctgagc cccggc UTI-Fc IgG1 3Ser d1 Protein sequence

SEQ ID NO: 25 avlpqeeegsgggqlvtevtkkedscqlgysagpcmgmtsryfyngtsmacetfqyggcmgngnnfvtekeclqtcrepkssd kthtcppcpapellggssvflfppkpkdtlmisrtpevtcvvvdvshedpevkfnwyvdgvevhnaktkpreeqynstyrvvsv ltvlhqdwlngkeykckvsnkalpasiektiskakgqprepqvytlppsreemtknqvsltclvkgfypsdiavewesngqpen nykttppvldsdgsfflysklvtdksrwqqgnvfscsvmhealhnhytqkslslspg UTI-Fc IgG1 3Ser d1 DNA sequence

SEQ ID NO: 26 gctgtgctgcctcaggaagaggaaggctctggcggaggccagctcgtgaccgaagtgaccaagaaagaggactcctgccagctgg gctactctgccggcccttgtatgggcatgacctcccggtacttctacaacggcacctccatggcctgcgagacattccagtacggcgg ctgcatgggcaacggcaacaacthgtgacagagaaagagtgcctgcagacctgcagagagcccaaatcttccgacaagacccata cctgtccaccttgccctgcccccgagctgctgggaggatcctctgtgttcctgttccccccaaagcccaaggacaccctgatgatctcc cggacccctgaagtgacctgcgtggtggtggatgtgtcccacgaggatcccgaagtgaagttcaattggtacgtggacggcgtggaa gtgcacaacgccaagaccaagcccagagaggaacagtacaactccacctaccgggtggtgtccgtgctgaccgtgctgcaccagg attggctgaacggcaaagagtacaagtgcaaggtgtccaacaaggccctgcctgcctccatcgaaaagaccatctccaaggccaag -continued ggccagccccgggaaccccaggtgtacacactgcccctagccgggaagagatgacaaagaaccaggtgtccctgacctgtctcgt gaagggattctaccctccgatatcgccgtggaatgggagtccaacggccagcctgagaacaactacaagaccaccccctgtgct ggactccgacggctcattcttcctgtactccaagctgacagtggacaagtcccggtggcagcagggcaacgtgttctcctgctccgtga tgcacgaggccctgcacaaccactacacccagaagtccctgtccctgagccccggc mUTI-mFc mIgG1 Protein sequence
SEQ ID NO: 27 avlpqesegsgteplitgtlkkedscqlnysegpclgmqeryyyngasmacetfqyggclgngnnfisekdclqtcrtiaacnlpiv qgperafiklwafdaaqgkciqfhyggckgngnkfysekeckeycgvpgdgyeelirskivprdcgkpcictvpevssvfifp pkpkdvltitltpkvtcvvvdiskddpevqfswfvddvevhtaqtqpreeqfnstfrsvselpimhqdwlngkefkcrvnsaafp apiektisktkgrpkapqvytipppkeqmakdkvsltcmitdffpeditvewqwngqpaenykntqpimdtdgsyfvysklnv qksnweagntftcsvlheglhnhhtekslshspgk mUTI-mFc mIgG1 DNA sequence
SEQ ID NO: 28 gcagtgctgccccaagagagtgaggggtcagggactgagccactaataactgggaccctcaagaagaagactcctgccagctcaa ttactcagaaggcccctgcctaggatgcaagagaggtattactacaacggcgcttccatggcctgcgagacctttcaatatggggtt gcctaggcaacggcaacaacttcatctctgagaaggactgtctgcagacatgtcggaccatagcggcctgcaatctccccatagtcca aggcccctgccgagccttcataaagctctgggcatttgatgcagcacaagggaagtgcatccaattccactacggggctgcaaagg caacggcaacaaattctactctgagaaggaatgcaaagagtactgtggagtccctggtgatgggtacgaggaactaatacgcagtaaa atcgtgcctcgggactgcggctgcaagccctgcatctgcaccgtgcccgaggtgtcctccgtgttcatcttcccacccaagcccaagg acgtgctgaccatcaccctgaccccccaaagtgacctgcgtggtggtggacatctccaaggacgaccccgaggtgcagttcagttggtt cgtggacgacgtggaagtgcacaccgcccagacccagcccagagaggaacagttcaactccaccttcagatccgtgtccgagctgc ccatcatgcaccaggactggctgaacggcaaagagttcaagtgcagagtgaactccgccgccttcccagcccccatcgaaaagacc atctccaagaccaagggcagacccaaggccccccaggtgtacaccatcccccaccaaagaacagatggcaaggacaaggtgt ccctgacctgcatgatcaccgatttcttcccagaggacatcaccgtggaatggcagtggaacggccagcccgccgagaactacaaga cacccagcccatcatggacaccgacggctcctacttcgtgtactccaagctgaacgtgcagaagtccaactgggaggccggcaac accttcacctgtagcgtgctgcacgagggcctgcacaaccaccacaccgagaagtccctgtcccactcccccggcaag Fc IgG1 3Ser UTI Protein sequence
SEQ ID NO: 29 epkssdkthtcppcpapellggssvflfppkpkdtlmisrtpevtcvvvdvshedpevkfnwyvdgvevhnaktkpreeqynst yrvvsvltvlhqdwlngkeykckvsnkalpasiektiskakgqprepqvytlppsreemtknqvsltclvkgfypsdiavewesn gqpennykttppvldsdgsfflysklt vdksrwqqgnvfscsvmhealhnhytqkslslspgkggggsggggsggggsavlpq eeegsgggqlvtevtkkedscqlgysagpcmgmtsryfyngtsmacetfqyggcmgngnnfvtekeclqtcrtvaacnlpivrg pcrafiqlwafdavkgkcvlfpyggcqgngnkfysekecreycgvpgdgdeellr Fc IgG1 3Ser UTI DNA sequence
SEQ ID NO: 30 gagcccaaatcttccgacaagacccatacctgtccaccttgccctgcccccgagctgctgggaggatcctctgtgttcctgttccccc aaagcccaaggacaccctgatgatctcccggacccctgaagtgacctgcgtggtggtggatgtgtcccacgaggatcccgaagtgaa gttcaattggtacgtggacggcgtggaagtgcacaacgccaagaccaagccagagaggaacagtacaactccacctaccgggtg gtgtccgtgctgaccgtgctgcaccaggattggctgaacggcaaagagtacaagtgcaaggtgtccaacaaggcctgcctgcctcc atcgaaaagaccatctccaaggccaagggccagcccggaaccccaggtgtacacactgcccctagccgggaagagatgaca aagaaccaggtgtccctgacctgtctcgtgaagggattctaccctccgatatcgccgtggaatgggagtccaacggccagcctgag aacaactacaagaccaccccccctgtgctggactccgacggctcattcttcctgtactccaagctgacagtggacaagtcccggtggc agcagggcaacgtgttctcctgctccgtgatgcacgaggccctgcacaaccactacacccagaagtccctgtccctgagccccggca agggaggtggtggatcaggaggtggaggttccggtggcggaggatcagctgtgctgcctcaggaagaggaaggctctggcggag gccagctcgtgaccgaagtgaccaagaaagaggactcctgccagctgggctactctgccggcccttgtatgggcatgacctcccggt

```
acttctacaacggcacctccatggcctgcgagacattccagtacggcggctgcatgggcaacggcaacaactttgtgacagagaaag agtgcctgcagacctgcagaaccgtggccgcctgtaacctgcctatcgtgcggggaccctgtcgggcctttatccagctgtgggcctt cgacgccgtgaagggcaaatgcgtgctgttccccctatggcggctgccagggaaatggaaacaagttctactccgagaaagaatgcc gcgagtactgtggcgtgccaggcgacggggatgaggaactgctgcgg
``` hUTI protein sequence      SEQ ID NO: 31

```
avipq eeegsggggl vtevtkkeds cqlgysagpc mgmtsryfyn gtsmacetfq yggcmgngnn fvtekeclqt crtvaacnlp ivrgperafi qlwafdavkg kcvlfpyggc qgngnkfyse kecreycgvp gdgdeellrf sn
```

AMBP preproprotein sequence      SEQ ID NO: 32

```
mrslgalll lsaclavsag pvptppdniq vqenfnisri ygkwynlaig stcpwlkkim drmtvstlvl gegateaeis mtstrwrkgv ceetsgayek tdtdgkflyh kskwnitmes yvvhtnydey aifltkkfsr hhgptitakl ygrapqlret llqdfrvvaq gvgipedsif tmadrgecvp geqepepili prvrravlpq eeegsggggl vtevtkkeds cqlgysagpc mgmtsryfyn gtsmacetfq yggcmgngnn fvtekeclqt crtvaacnlp ivrgperafi qlwafdavkg kcvlfpyggc qgngnkfyse kecreycgvp gdgdeellrf sn
```

SGGGGS      SEQ ID NO: 33

SGGGGSGGGGS      SEQ ID NO: 34

SGGGGSGGGGSGGGGS      SEQ ID NO: 35

SGGGGSGGGGSGGGGSGGGGS      SEQ ID NO: 36

SGGGGSGGGGSGGGGSGGGGSGGGGS      SEQ ID NO: 37

SGGGGSGGGGSGGGGSGGGGSGGGGSGGGGS      SEQ ID NO: 38

SGGGGSGGGGSGGGGSGGGGSGGGGSGGGGSGGGGS      SEQ ID NO: 39

SGGGGSGGGGSGGGGSGGGGSGGGGSGGGGSGGGGSGGGGS      SEQ ID NO: 40

SGGGGSGGGGSGGGGSGGGGSGGGGSGGGGSGGGGSGGGGSGGGGS      SEQ ID NO: 41

SGGGGSGGGGSGGGGSGGGGSGGGGSGGGGSGGGGSGGGGSGGGGSGGGGS      SEQ ID NO: 42

GSGGGSGGGGSGGGGS      SEQ ID NO: 43

---

What is claimed is:

1. An isolated urinary trypsin inhibitor (UTI) fusion protein comprising amino acids 1 to 149 of SEQ ID NO:1 linked to a wild-type Fc domain, wherein the Fc domain excludes the first constant region immunoglobulin domain, or fragment thereof that does not contain one or more substitutions.

2. A dimer comprising two isolated urinary trypsin inhibitor (UTI) fusion proteins of claim 1, wherein the Fc domains, or fragments thereof, are associated covalently.

3. The isolated UTI fusion protein of claim 1 or the dimer of claim 2 wherein the Fc domain is selected from the group consisting of an IgG1, an IgG2 and an IgG4 Fc domain.

4. The isolated UTI fusion protein of claim 1 or the dimer of claim 2, wherein the Fc domain is an IgG1 Fc domain.

5. A pharmaceutical composition comprising the UTI fusion protein of claim 1 or the dimer of claim 2, and a pharmaceutically acceptable excipient.

6. A nucleic acid encoding the UTI fusion protein of claim 1 or the dimer of claim 2.

7. An expression vector comprising the nucleic acid of claim 6.

8. A recombinant host cell comprising the expression vector of claim 7.

9. The recombinant host cell of claim 8, wherein the cell is selected from the group consisting of a mammalian cell, an insect cell, an E. coli cell, a yeast cell, and a plant cell.

10. The recombinant host cell of claim 9, wherein the mammalian cell is selected from the group consisting of a Chinese hamster ovary (CHO) cell, an HEK 293 cell, an NSO cell, a HeLa cell, a baby hamster kidney (BHK) cell, a monkey kidney cell (COS) and a human hepatocellular carcinoma cell.

11. A method of treating a UTI-related condition comprising administering to a patient in need thereof an effective amount of the UTI fusion protein of claim 1 or the dimer of claim 2.

12. The method of claim 11, wherein the UTI-related condition is selected from the group consisting of pancreatitis, arthritis, SARS, systemic inflammatory response syndrome, acute circulatory failure, sepsis, hepatitis, appendicitis, colitis, organ failure, organ damage, reperfusion injury, Stevens-Johnson syndrome, toxic epidermal necrolysis, shock, ischemic injuries, acute lung injury, asthma, lung inflammation, pneumonia, disseminated intravascular coagulation, and acute respiratory distress syndrome.

13. The method of claim 11, wherein the UTI-related condition is acute pancreatitis.

14. The method of claim 11, wherein the UTI-related condition is selected from the group consisting of endoscopy induced pancreatitis, pancreas damage, kidney damage, lung damage, lung injury caused by acute aortic dissection, and ventilator associated pneumonia.

15. A method of producing a urinary trypsin inhibitor (UTI) fusion protein, comprising placing the recombinant host cell of claim 8 in a growth medium such that a recombinant fusion protein is expressed, and isolating the recombinant fusion protein from the cell or growth medium.

16. A method of producing a UTI fusion protein, wherein the UTI fusion protein of claim 1 or the dimer of claim 2 is produced in a transgenic animal.

* * * * *

SEQUENCE LISTING

<160> NUMBER OF SEQ ID NOS: 48

<210> SEQ ID NO 1
<211> LENGTH: 375
<212> TYPE: PRT
<213> ORGANISM: Artificial Sequence
<220> FEATURE:
<221> NAME/KEY: source
<223> OTHER INFORMATION: /note="Description of Artificial Sequence:
        Synthetic polypeptide"

```
<400> SEQUENCE: 1

Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
                20                  25                  30

Gly Pro Cys Met Gly Met Thr Ser Arg Tyr Phe Tyr Asn Gly Thr Ser
            35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
            115                 120                 125

Arg Glu Tyr Cys Gly Val Pro Gly Asp Gly Asp Glu Glu Leu Leu Gly
            130                 135                 140

Ser Gly Gly Gly Gly Asp Lys Thr His Thr Cys Pro Pro Cys Pro Ala
145                 150                 155                 160

Pro Glu Leu Leu Gly Gly Pro Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
            195                 200                 205

Asp Gly Val Glu Val His Asn Ala Lys Thr Lys Pro Arg Glu Glu Gln
210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Pro Ile Glu Lys Thr Ile Ser Lys Ala Lys Gly Gln Pro
            260                 265                 270

Arg Glu Pro Gln Val Tyr Thr Leu Pro Pro Ser Arg Glu Glu Met Thr
            275                 280                 285

Lys Asn Gln Val Ser Leu Thr Cys Leu Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
            355                 360                 365

Ser Leu Ser Leu Ser Pro Gly
    370                 375

<210> SEQ ID NO 2
<211> LENGTH: 1125
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic polynucleotide"

<400> SEQUENCE: 2
gctgtgctgc ctcaggaaga ggaaggctct ggcggaggcc agctcgtgac cgaagtgacc        60
aagaaagagg actcctgcca gctgggctac tctgccggcc cttgtatggg catgacctcc       120
cggtacttct acaacggcac ctccatggcc tgcgagacat tccagtacgg cggctgcatg       180
ggcaacggca caactttgt gacagagaaa gagtgcctgc agacctgcag aaccgtggcc        240
gcctgtaacc tgcctatcgt gcggggaccc tgtcgggcct ttatccagct gtgggccttc       300
gacgccgtga agggcaaatg cgtgctgttc ccctatggcg gctgccaggg aaatggaaac       360
aagttctact ccgagaaaga atgccgcgag tactgtggcg tgccaggcga cggggatgag       420
gaactgctgg gatcaggcgg cggaggcgac aagacccata cctgtccacc ttgccctgcc       480
cccgagctgc tggaggacc ttctgtgttc ctgttccccc caaagcccaa ggacaccctg        540
atgatctccc ggacccctga agtgacctgc gtggtggtgg atgtgtccca cgaggatccc       600
gaagtgaagt tcaattggta cgtggacggc gtggaagtgc acaacgccaa gaccaagccc       660
agagaggaac agtacaactc cacctaccgg gtggtgtccg tgctgaccgt gctgcaccag       720
gattggctga acggcaaaga gtacaagtgc aaggtgtcca acaaggccct gcctgccccc       780
atcgaaaaga ccatctccaa ggccaagggc cagccccggg aaccccaggt gtacacactg       840
ccccctagcc gggaagagat gacaaagaac caggtgtccc tgacctgtct cgtgaaggga       900 ttctaccccct ccgatatcgc cgtggaatgg gagtccaacg ccagcctga aacaactac        960 aagaccaccc cccctgtgct ggactccgac ggctcattct tcctgtactc caagctgaca      1020
gtggacaagt cccggtggca gcaggcaac gtgttctcct gctccgtgat gcacgaggcc       1080
ctgcacaacc actacaccca gaagtccctg tccctgagcc ccggc                     1125

<210> SEQ ID NO 3
<211> LENGTH: 375
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Ala Val Leu Pro Gln Glu Glu Glu Gly Ser Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
```

```
            115                 120                 125
Arg Glu Tyr Cys Gly Val Pro Gly Asp Gly Asp Glu Glu Leu Leu Arg
    130                 135                 140

Glu Pro Lys Ser Ser Asp Lys Thr His Thr Cys Pro Pro Cys Pro Ala
145                 150                 155                 160

Pro Glu Leu Leu Gly Gly Ser Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Ser Ile Glu Lys Thr Ile Ser Lys Ala Lys Gly Gln Pro
            260                 265                 270

Arg Glu Pro Gln Val Tyr Thr Leu Pro Pro Ser Arg Glu Glu Met Thr
        275                 280                 285

Lys Asn Gln Val Ser Leu Thr Cys Leu Val Lys Gly Phe Tyr Pro Ser
290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly
    370                 375

<210> SEQ ID NO 4
<211> LENGTH: 1125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 4
gctgtgctgc ctcaggaaga ggaaggctct ggcggaggcc agctcgtgac cgaagtgacc      60
aagaaagagg actcctgcca gctgggctac tctgccggcc cttgtatggg catgacctcc     120
cggtacttct acaacggcac ctccatggcc tgcgagacat ccagtacgg cggctgcatg     180 ggcaacggca caactttgt gacagagaaa gagtgcctgc agacctgcag aaccgtggcc     240
gcctgtaacc tgcctatcgt gcggggaccc tgtcgggcct ttatccagct gtgggccttc     300
gacgccgtga agggcaaatg cgtgctgttc ccctatggcg gctgccaggg aaatggaaac     360
aagttctact ccgagaaaga atgccgcgag tactgtggcg tgccaggcga cggggatgag     420
gaactgctgc gggagcccaa atcttccgac aagacccata cctgtccacc ttgccctgcc     480
cccgagctgc tgggaggatc ctctgtgttc ctgttccccc caaagcccaa ggacaccctg     540
```

```
atgatctccc ggacccctga agtgacctgc gtggtggtgg atgtgtccca cgaggatccc    600
gaagtgaagt tcaattggta cgtggacggc gtggaagtgc acaacgccaa gaccaagccc    660
agagaggaac agtacaactc cacctaccgg gtggtgtccg tgctgaccgt gctgcaccag    720
gattggctga acggcaaaga gtacaagtgc aaggtgtcca acaaggccct gcctgcctcc    780
atcgaaaaga ccatctccaa ggccaagggc cagccccggg aaccccaggt gtacacactg    840
cccccuagcc gggaagagat gacaaagaac caggtgtccc tgacctgtct cgtgaaggga    900
ttctacccct ccgatatcgc cgtggaatgg gagtccaacg gccagcctga gaacaactac    960
aagaccaccc cccctgtgct ggactccgac ggctcattct tcctgtactc caagctgaca   1020
gtggacaagt cccggtggca gcagggcaac gtgttctcct gctccgtgat gcacgaggcc   1080
ctgcacaacc actacaccca gaagtccctg tccctgagcc ccggc                  1125
```

<210> SEQ ID NO 5
<211> LENGTH: 370
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 5

```
Ala Val Leu Pro Gln Glu Glu Glu Gly Ser Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Arg
    130                 135                 140

Lys Ser Cys Val Glu Cys Pro Pro Cys Pro Ala Pro Pro Val Ala Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Gln Phe Asn Trp Tyr Val Asp Gly Met Glu Val His
        195                 200                 205

Asn Ala Lys Thr Lys Pro Arg Glu Glu Gln Phe Asn Ser Thr Phe Arg
    210                 215                 220

Val Val Ser Val Leu Thr Val Val His Gln Asp Trp Leu Asn Gly Lys
225                 230                 235                 240

Glu Tyr Lys Cys Lys Val Ser Asn Lys Gly Leu Pro Ala Pro Ile Glu
```

```
                  245                 250                 255
Lys Thr Ile Ser Lys Thr Lys Gly Gln Pro Arg Glu Pro Gln Val Tyr
            260                 265                 270

Thr Leu Pro Pro Ser Arg Glu Glu Met Thr Lys Asn Gln Val Ser Leu
        275                 280                 285

Thr Cys Leu Val Lys Gly Phe Tyr Pro Ser Asp Ile Ala Val Glu Trp
    290                 295                 300

Glu Ser Asn Gly Gln Pro Glu Asn Asn Tyr Lys Thr Thr Pro Pro Met
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
                340                 345                 350

Glu Ala Leu His Asn His Tyr Thr Gln Lys Ser Leu Ser Leu Ser Pro
            355                 360                 365

Gly Lys
    370

<210> SEQ ID NO 6
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
gctgtgctgc tcaggaaga ggaaggctct ggcggaggcc agctcgtgac cgaagtgacc      60
aagaaagagg actcctgcca gctgggctac tctgccggcc cttgtatggg catgaccctcc    120 cggtacttct acaacggcac ctccatggcc tgcgagacat ccagtacgg cggctgcatg      180 ggcaacggca caactttgt gacagagaaa gagtgcctgc agacctgcag aaccgtggcc      240
gcctgtaacc tgcctatcgt gcggggaccc tgtcgggcct ttatccagct gtgggccttc     300
gacgccgtga agggcaaatg cgtgctgttc ccctatggcg gctgccaggg aaatggaaac     360
aagttctact ccgagaaaga tgccgcgag tactgtggcg tgccaggcga cggggatgag      420
gaactgctgc ggaaatcctg tgtcgagtgc caccgtgcc cagcaccacc tgtggcagga     480
ccgtcagtct tcctcttccc cccaaaaccc aaggacaccc tcatgatctc ccggacccct    540
gaggtcacgt gcgtggtggt ggacgtgagc cacgaagacc ccgaggtcca gttcaactgg    600
tacgtggacg gcatggaggt gcataatgcc aagacaaagc cacgggagga gcagttcaac    660
agcacgttcc gtgtggtcag cgtcctcacc gtcgtgcacc aggactggct gaacggcaag    720
gagtacaagt gcaaggtctc caacaaaggc ctcccagccc catcgagaa aaccatctcc     780 aaaaccaaag gcagccccg agaaccacag gtgtacaccc tgcccccatc ccggaggag      840 atgaccaaga accaggtcag cctgacctgc ctggtcaaag gcttctaccc cagcgacatc    900
gccgtggagt gggagagcaa tgggcagccg gagaacaact acaagaccac cctcccatg    960 ctggactccg acggctcctt cttcctctac agcaagctca ccgtggacaa gagcaggtgg    1020
cagcagggga acgtcttctc atgctccgtg atgcatgagg ctctgcacaa ccactacaca    1080
cagaagagcc tctccctgtc tccgggtaaa                                     1110

<210> SEQ ID NO 7
<211> LENGTH: 370
```

<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 7

```
Ala Val Leu Pro Gln Glu Glu Gly Ser Gly Gly Gln Leu Val
1               5                   10                  15

Thr Glu Val Thr Lys Lys Glu Asp Ser Cys Gln Leu Gly Tyr Ser Ala
                20                  25                  30

Gly Pro Cys Met Gly Met Thr Ser Arg Tyr Phe Tyr Asn Gly Thr Ser
            35                  40                  45

Met Ala Cys Glu Thr Phe Gln Tyr Gly Gly Cys Met Gly Asn Gly Asn
50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
            115                 120                 125

Arg Glu Tyr Cys Gly Val Pro Gly Asp Gly Asp Glu Glu Leu Leu Arg
130                 135                 140

Lys Cys Cys Val Glu Cys Pro Pro Cys Pro Ala Pro Pro Val Ala Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Gln Phe Asn Trp Tyr Val Asp Gly Met Glu Val His
            195                 200                 205

Asn Ala Lys Thr Lys Pro Arg Glu Glu Gln Phe Asn Ser Thr Phe Arg
210                 215                 220

Val Val Ser Val Leu Thr Val Val His Gln Asp Trp Leu Asn Gly Lys
225                 230                 235                 240

Glu Tyr Lys Cys Lys Val Ser Asn Lys Gly Leu Pro Ala Pro Ile Glu
                245                 250                 255

Lys Thr Ile Ser Lys Thr Lys Gly Gln Pro Arg Glu Pro Gln Val Tyr
            260                 265                 270

Thr Leu Pro Pro Ser Arg Glu Glu Met Thr Lys Asn Gln Val Ser Leu
            275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Met
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
            355                 360                 365

Gly Lys
```

<210> SEQ ID NO 8
<211> LENGTH: 1110
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 8

```
gctgtgctgc ctcaggaaga ggaaggctct ggcggaggcc agctcgtgac cgaagtgacc      60
aagaaagagg actcctgcca gctgggctac tctgccggcc cttgtatggg catgacctcc     120
cggtacttct acaacggcac ctccatggcc tgcgagacat tccagtacgg cggctgcatg     180
ggcaacggca acaactttgt gacagagaaa gagtgcctgc agacctgcag aaccgtggcc     240
gcctgtaacc tgcctatcgt gcggggaccc tgtcgggcct ttatccagct gtgggccttc     300
gacgccgtga agggcaaatg cgtgctgttc ccctatggcg gctgccaggg aaatggaaac     360
aagttctact ccgagaaaga atgccgcgag tactgtggcg tgccaggcga cggggatgag     420
gaactgctgc ggaaatgttg tgtcgagtgc caccgtgcc cagcaccacc tgtggcagga     480
ccgtcagtct tcctcttccc cccaaaaccc aaggacaccc tcatgatctc ccggacccct     540
gaggtcacgt gcgtggtggt ggacgtgagc acgaagacc ccgaggtcca gttcaactgg     600
tacgtggacg gcatggaggt gcataatgcc aagacaaagc cacgggagga gcagttcaac     660
agcacgttcc gtgtggtcag cgtcctcacc gtcgtgcacc aggactggct gaacggcaag     720
gagtacaagt gcaaggtctc caacaaaggc ctcccagccc ccatcgagaa aaccatctcc     780
aaaaccaaag gcagccccg agaaccacag gtgtacaccc tgcccccatc ccggaggag      840
atgaccaaga accaggtcag cctgacctgc ctggtcaaag gcttctaccc cagcgacatc     900
gccgtggagt gggagagcaa tgggcagccg gagaacaact acaagaccac acctcccatg     960
ctggactccg acggctcctt cttcctctac agcaagctca ccgtggacaa gagcaggtgg    1020
cagcagggga acgtcttctc atgctccgtg atgcatgagg ctctgcacaa ccactacaca    1080
cagaagagcc tctccctgtc tccgggtaaa                                    1110
```

<210> SEQ ID NO 9
<211> LENGTH: 375
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 9

```
Ala Val Leu Pro Gln Glu Glu Glu Gly Ala Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80
```

```
Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Arg
    130                 135                 140

Glu Pro Lys Ser Ser Asp Lys Thr His Thr Cys Pro Pro Cys Pro Ala
145                 150                 155                 160

Pro Glu Leu Leu Gly Gly Ser Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Ser Ile Glu Lys Thr Ile Ser Lys Ala Lys Gly Gln Pro
            260                 265                 270

Arg Glu Pro Gln Val Tyr Thr Leu Pro Pro Ser Arg Glu Glu Met Thr
        275                 280                 285

Lys Asn Gln Val Ser Leu Thr Cys Leu Val Lys Gly Phe Tyr Pro Ser
    290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
        355                 360                 365

Ser Leu Ser Leu Ser Pro Gly
    370                 375

<210> SEQ ID NO 10
<211> LENGTH: 1125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 10
gctgtgctgc ctcaggaaga ggaaggcgca ggcggaggcc agctcgtgac cgaagtgacc      60
aagaaagagg actcctgcca gctgggctac tctgccggcc cttgtatggg catgacctcc     120
cggtacttct acaacggcac ctccatggcc tgcgagacat tccagtacgg cggctgcatg     180
ggcaacggca caactttgt gacagagaaa gagtgcctgc agacctgcag aaccgtggcc      240
gcctgtaacc tgcctatcgt gcggggaccc tgtcgggcct ttatccagct gtgggccttc     300
```

-continued

```
gacgccgtga agggcaaatg cgtgctgttc ccctatggcg gctgccaggg aaatggaaac      360
aagttctact ccgagaaaga atgccgcgag tactgtggcg tgccaggcga cggggatgag      420
gaactgctgc gggagcccaa atcttccgac aagacccata cctgtccacc ttgccctgcc      480
cccgagctgc tggaggatc ctctgtgttc ctgttccccc caaagcccaa ggacaccctg      540
atgatctccc ggaccectga agtgacctgc gtggtggtgg atgtgtccca cgaggatccc      600
gaagtgaagt tcaattggta cgtggacggc gtggaagtgc acaacgccaa gaccaagccc      660
agagaggaac agtacaactc cacctaccgg gtggtgtccg tgctgaccgt gctgcaccag      720
gattggctga acggcaaaga gtacaagtgc aaggtgtcca acaaggccct gcctgcctcc      780
atcgaaaaga ccatctccaa ggccaagggc cagccccggg aaccccaggt gtacacactg      840 cccctagcc gggaagagat gacaaagaac caggtgtccc tgacctgtct cgtgaaggga      900
ttctacccct ccgatatcgc cgtggaatgg gagtccaacg gccagcctga gaacaactac      960
aagaccaccc cccctgtgct ggactccgac ggctcattct tcctgtactc caagctgaca     1020
gtggacaagt cccggtggca gcagggcaac gtgttctcct gctccgtgat gcacgaggcc     1080
ctgcacaacc actacaccca gaagtccctg tccctgagcc ccggc                     1125
```

<210> SEQ ID NO 11
<211> LENGTH: 353
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 11

```
Glu Asp Ser Cys Gln Leu Gly Tyr Ser Ala Gly Pro Cys Met Gly Met
1               5                   10                  15

Thr Ser Arg Tyr Phe Tyr Asn Gly Thr Ser Met Ala Cys Glu Thr Phe
            20                  25                  30

Gln Tyr Gly Gly Cys Met Gly Asn Gly Asn Asn Phe Val Thr Glu Lys
        35                  40                  45

Glu Cys Leu Gln Thr Cys Arg Thr Val Ala Ala Cys Asn Leu Pro Ile
    50                  55                  60

Val Arg Gly Pro Cys Arg Ala Phe Ile Gln Leu Trp Ala Phe Asp Ala
65                  70                  75                  80

Val Lys Gly Lys Cys Val Leu Phe Pro Tyr Gly Gly Cys Gln Gly Asn
                85                  90                  95

Gly Asn Lys Phe Tyr Ser Glu Lys Glu Cys Arg Glu Tyr Cys Gly Val
            100                 105                 110

Pro Gly Asp Gly Asp Glu Glu Leu Leu Arg Glu Pro Lys Ser Ser Asp
        115                 120                 125

Lys Thr His Thr Cys Pro Pro Cys Pro Ala Pro Glu Leu Leu Gly Gly
    130                 135                 140

Ser Ser Val Phe Leu Phe Pro Pro Lys Pro Lys Asp Thr Leu Met Ile
145                 150                 155                 160

Ser Arg Thr Pro Glu Val Thr Cys Val Val Val Asp Val Ser His Glu
                165                 170                 175

Asp Pro Glu Val Lys Phe Asn Trp Tyr Val Asp Gly Val Glu Val His
            180                 185                 190

Asn Ala Lys Thr Lys Pro Arg Glu Glu Gln Tyr Asn Ser Thr Tyr Arg
        195                 200                 205
```

```
Val Val Ser Val Leu Thr Val Leu His Gln Asp Trp Leu Asn Gly Lys
    210                 215                 220
Glu Tyr Lys Cys Lys Val Ser Asn Lys Ala Leu Pro Ala Ser Ile Glu
225                 230                 235                 240
Lys Thr Ile Ser Lys Ala Lys Gly Gln Pro Arg Glu Pro Gln Val Tyr
                245                 250                 255
Thr Leu Pro Pro Ser Arg Glu Glu Met Thr Lys Asn Gln Val Ser Leu
            260                 265                 270
Thr Cys Leu Val Lys Gly Phe Tyr Pro Ser Asp Ile Ala Val Glu Trp
        275                 280                 285
Glu Ser Asn Gly Gln Pro Glu Asn Asn Tyr Lys Thr Thr Pro Pro Val
    290                 295                 300
Leu Asp Ser Asp Gly Ser Phe Phe Leu Tyr Ser Lys Leu Thr Val Asp
305                 310                 315                 320
Lys Ser Arg Trp Gln Gln Gly Asn Val Phe Ser Cys Ser Val Met His
                325                 330                 335
Glu Ala Leu His Asn His Tyr Thr Gln Lys Ser Leu Ser Leu Ser Pro
            340                 345                 350
Gly

<210> SEQ ID NO 12
<211> LENGTH: 1059
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 12
gaggactcct gccagctggg ctactctgcc ggcccttgta tgggcatgac ctcccggtac     60
ttctacaacg gcacctccat ggcctgcgag acattccagt acggcggctg catgggcaac    120
ggcaacaact ttgtgacaga gaaagagtgc ctgcagacct gcagaaccgt ggccgcctgt    180
aacctgccta tcgtgcgggg accctgtcgg gcctttatcc agctgtgggc cttcgacgcc    240
gtgaagggca atgcgtgct gttcccctat ggcggctgcc agggaaatgg aaacaagttc    300
tactccgaga agaatgccg cgagtactgt ggcgtgccag cgacggggga tgaggaactg    360
ctgcgggagc ccaaatcttc cgacaagacc catacctgtc caccttgccc tgcccccgag    420
ctgctgggag atcctctgt gttcctgttc cccccaaagc ccaaggacac cctgatgatc    480
tcccggaccc ctgaagtgac ctgcgtggtg gtggatgtgt cccacgagga tcccgaagtg    540
aagttcaatt ggtacgtgga cggcgtggaa gtgcacaacg ccaagaccaa gccagagag    600 gaacagtaca actccaccta ccgggtggtg tccgtgctga ccgtgctgca ccaggattgg    660
ctgaacggca agagtacaa gtgcaaggtg tccaacaagg ccctgcctgc ctccatcgaa    720
aagaccatct ccaaggccaa gggccagccc cgggaacccc aggtgtacac actgcccct     780 agccgggaag agatgacaaa gaaccaggtg tccctgacct gtctcgtgaa gggattctac    840
ccctccgata tcgccgtgga atgggagtcc aacggccagc ctgagaacaa ctacaagacc    900 acccccctg tgctggactc cgacggctca ttcttcctgt actccaagct gacagtggac    960
aagtcccggt ggcagcaggg caacgtgttc tcctgctccg tgatgcacga ggccctgcac   1020
aaccactaca cccagaagtc cctgtccctg agccccggc                          1059

<210> SEQ ID NO 13
```

<211> LENGTH: 253
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 13

```
Ala Val Leu Pro Gln Glu Glu Glu Gly Ser Gly Gly Gly Gln Leu Val
1               5                   10                  15

Thr Glu Val Thr Lys Lys Glu Pro Lys Ser Ser Asp Lys Thr His Thr
            20                  25                  30

Cys Pro Pro Cys Pro Ala Pro Glu Leu Leu Gly Gly Ser Ser Val Phe
        35                  40                  45

Leu Phe Pro Pro Lys Pro Lys Asp Thr Leu Met Ile Ser Arg Thr Pro
    50                  55                  60

Glu Val Thr Cys Val Val Val Asp Val Ser His Glu Asp Pro Glu Val
65                  70                  75                  80

Lys Phe Asn Trp Tyr Val Asp Gly Val Glu Val His Asn Ala Lys Thr
                85                  90                  95

Lys Pro Arg Glu Glu Gln Tyr Asn Ser Thr Tyr Arg Val Val Ser Val
            100                 105                 110

Leu Thr Val Leu His Gln Asp Trp Leu Asn Gly Lys Glu Tyr Lys Cys
        115                 120                 125

Lys Val Ser Asn Lys Ala Leu Pro Ala Ser Ile Glu Lys Thr Ile Ser
    130                 135                 140

Lys Ala Lys Gly Gln Pro Arg Glu Pro Gln Val Tyr Thr Leu Pro Pro
145                 150                 155                 160

Ser Arg Glu Glu Met Thr Lys Asn Gln Val Ser Leu Thr Cys Leu Val
                165                 170                 175

Lys Gly Phe Tyr Pro Ser Asp Ile Ala Val Glu Trp Glu Ser Asn Gly
            180                 185                 190

Gln Pro Glu Asn Asn Tyr Lys Thr Thr Pro Pro Val Leu Asp Ser Asp
        195                 200                 205

Gly Ser Phe Phe Leu Tyr Ser Lys Leu Thr Val Asp Lys Ser Arg Trp
    210                 215                 220

Gln Gln Gly Asn Val Phe Ser Cys Ser Val Met His Glu Ala Leu His
225                 230                 235                 240

Asn His Tyr Thr Gln Lys Ser Leu Ser Leu Ser Pro Gly
                245                 250
```

<210> SEQ ID NO 14
<211> LENGTH: 759
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
gctgtgctgc ctcaggaaga ggaaggctct ggcggaggcc agctcgtgac cgaagtgacc    60
aagaaagagc ccaaatcttc cgacaagacc catacctgtc caccttgccc tgccccccgag   120 ctgctgggag gatcctctgt gttcctgttc ccccccaaagc ccaaggacac cctgatgatc   180
tcccggaccc ctgaagtgac ctgcgtggtg gtggatgtgt cccacgagga tcccgaagtg   240
aagttcaatt ggtacgtgga cggcgtggaa gtgcacaacg ccaagaccaa gcccagagag   300
```

```
gaacagtaca actccaccta ccgggtggtg tccgtgctga ccgtgctgca ccaggattgg    360
ctgaacggca agagtacaa gtgcaaggtg tccaacaagg ccctgcctgc ctccatcgaa    420
aagaccatct ccaaggccaa gggccagccc cgggaacccc aggtgtacac actgcccct    480 agccgggaag atgacaaa gaaccaggtg tccctgacct gtctcgtgaa gggattctac    540
ccctccgata tcgccgtgga atgggagtcc aacggccagc ctgagaacaa ctacaagacc    600 accccctg tgctggactc cgacggctca ttcttcctgt actccaagct gacagtggac    660
aagtcccggt ggcagcaggg caacgtgttc tcctgctccg tgatgcacga ggccctgcac    720
aaccactaca cccagaagtc cctgtccctg agccccggc                          759
```

```
<210> SEQ ID NO 15
<211> LENGTH: 384
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Ala Val Leu Pro Gln Glu Glu Glu Gly Ser Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Gly
    130                 135                 140

Gly Gly Gly Ser Gly Gly Gly Ser Glu Pro Lys Ser Ser Asp Lys
145                 150                 155                 160

Thr His Thr Cys Pro Pro Cys Pro Ala Pro Glu Leu Leu Gly Gly Ser
                165                 170                 175

Ser Val Phe Leu Phe Pro Pro Lys Pro Lys Asp Thr Leu Met Ile Ser
            180                 185                 190

Arg Thr Pro Glu Val Thr Cys Val Val Val Asp Val Ser His Glu Asp
        195                 200                 205

Pro Glu Val Lys Phe Asn Trp Tyr Val Asp Gly Val Glu Val His Asn
    210                 215                 220

Ala Lys Thr Lys Pro Arg Glu Glu Gln Tyr Asn Ser Thr Tyr Arg Val
225                 230                 235                 240

Val Ser Val Leu Thr Val Leu His Gln Asp Trp Leu Asn Gly Lys Glu
                245                 250                 255

Tyr Lys Cys Lys Val Ser Asn Lys Ala Leu Pro Ala Ser Ile Glu Lys
            260                 265                 270
```

Thr Ile Ser Lys Ala Lys Gly Gln Pro Arg Glu Pro Gln Val Tyr Thr
            275                 280                 285

Leu Pro Pro Ser Arg Glu Glu Met Thr Lys Asn Gln Val Ser Leu Thr
        290                 295                 300

Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Lys Leu Thr Val Asp Lys
            340                 345                 350

Ser Arg Trp Gln Gln Gly Asn Val Phe Ser Cys Ser Val Met His Glu
        355                 360                 365

Ala Leu His Asn His Tyr Thr Gln Lys Ser Leu Ser Leu Ser Pro Gly
    370                 375                 380

<210> SEQ ID NO 16
<211> LENGTH: 1152
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 16
gctgtgctgc tcaggaaga ggaaggctct ggcggaggcc agctcgtgac cgaagtgacc      60
aagaaagagg actcctgcca gctgggctac tctgccggcc cttgtatggg catgacctcc    120
cggtacttct acaacggcac ctccatggcc tgcgagacat ccagtacgg cggctgcatg     180 ggcaacggca caactttgt gacagagaaa gagtgcctgc agacctgcag aaccgtggcc     240
gcctgtaacc tgcctatcgt gcggggaccc tgtcgggcct ttatccagct gtgggccttc    300
gacgccgtga agggcaaatg cgtgctgttc ccctatggcg gctgccaggg aaatggaaac    360
aagttctact ccgagaaaga atgccgcgag tactgtggcg tgccaggcga cggggatgag    420
gaactgctgg aggtggtgg atcaggtggc ggaggatcag agcccaaatc ttccgacaag    480
acccatacct gtccaccttg ccctgccccc gagctgctgg aggatcctc tgtgttcctg    540 ttcccccaa agcccaagga caccctgatg atctcccgga cccctgaagt gacctgcgtg    600
gtggtggatg tgtcccacga ggatcccgaa gtgaagttca attggtacgt ggacggcgtg    660
gaagtgcaca cgccaagac caagcccaga gaggaacagt acaactccac ctaccgggtg    720
gtgtccgtgc tgaccgtgct gcaccaggat tggctgaacg gcaaagagta caagtgcaag    780
gtgtccaaca aggccctgcc tgcctccatc gaaaagacca ctccaaggc caagggccag    840 ccccgggaac ccaggtgta cacactgccc cctagccggg aagagatgac aaagaaccag    900
gtgtccctga cctgtctcgt gaagggattc taccctccg atatcgccgt ggaatgggag    960
tccaacggcc agcctgagaa caactacaag accacccccc ctgtgctgga ctccgacggc   1020
tcattcttcc tgtactccaa gctgacagtg gacaagtccc ggtggcagca gggcaacgtg   1080
ttctcctgct ccgtgatgca cgaggccctg cacaaccact acacccagaa gtccctgtcc   1140
ctgagccccg gc                                                       1152

<210> SEQ ID NO 17
<211> LENGTH: 365
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 17

Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
                35              40                  45

Met Ala Cys Glu Thr Phe Gln Tyr Gly Gly Cys Met Gly Asn Gly Asn
50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
            115                 120                 125

Arg Glu Tyr Cys Gly Val Pro Gly Asp Gly Asp Glu Glu Leu Leu Arg
            130                 135                 140

Cys Pro Pro Cys Pro Ala Pro Glu Leu Leu Gly Gly Ser Ser Val Phe
145                 150                 155                 160

Leu Phe Pro Pro Lys Pro Lys Asp Thr Leu Met Ile Ser Arg Thr Pro
                165                 170                 175

Glu Val Thr Cys Val Val Val Asp Val Ser His Glu Asp Pro Glu Val
            180                 185                 190

Lys Phe Asn Trp Tyr Val Asp Gly Val Glu Val His Asn Ala Lys Thr
            195                 200                 205

Lys Pro Arg Glu Glu Gln Tyr Asn Ser Thr Tyr Arg Val Val Ser Val
            210                 215                 220

Leu Thr Val Leu His Gln Asp Trp Leu Asn Gly Lys Glu Tyr Lys Cys
225                 230                 235                 240

Lys Val Ser Asn Lys Ala Leu Pro Ala Ser Ile Glu Lys Thr Ile Ser
                245                 250                 255

Lys Ala Lys Gly Gln Pro Arg Glu Pro Gln Val Tyr Thr Leu Pro Pro
            260                 265                 270

Ser Arg Glu Glu Met Thr Lys Asn Gln Val Ser Leu Thr Cys Leu Val
            275                 280                 285

Lys Gly Phe Tyr Pro Ser Asp Ile Ala Val Glu Trp Glu Ser Asn Gly
            290                 295                 300

Gln Pro Glu Asn Asn Tyr Lys Thr Thr Pro Pro Val Leu Asp Ser Asp
305                 310                 315                 320

Gly Ser Phe Phe Leu Tyr Ser Lys Leu Thr Val Asp Lys Ser Arg Trp
                325                 330                 335

Gln Gln Gly Asn Val Phe Ser Cys Ser Val Met His Glu Ala Leu His
            340                 345                 350

Asn His Tyr Thr Gln Lys Ser Leu Ser Leu Ser Pro Gly
            355                 360                 365

<210> SEQ ID NO 18
<211> LENGTH: 1095
```

<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 18

```
gctgtgctgc ctcaggaaga ggaaggctct ggcggaggcc agctcgtgac cgaagtgacc      60
aagaaagagg actcctgcca gctgggctac tctgccggcc cttgtatggg catgacctcc     120
cggtacttct acaacggcac ctccatggcc tgcgagacat tccagtacgg cggctgcatg     180
ggcaacggca caactttgt gacagagaaa gagtgcctgc agacctgcag aaccgtggcc      240
gcctgtaacc tgcctatcgt gcgggaccc tgtcgggcct ttatccagct gtgggccttc      300
gacgccgtga agggcaaatg cgtgctgttc ccctatggcg gctgccaggg aaatggaaac      360
aagttctact ccgagaaaga tgccgcgag tactgtggcg tgccaggcga cggggatgag      420
gaactgctgc ggtgtccacc ttgccctgcc ccgagctgc tgggaggatc ctctgtgttc      480
ctgttccccc caaagcccaa ggacaccctg atgatctccc ggaccctga agtgacctgc      540
gtggtggtgg atgtgtccca cgaggatccc gaagtgaagt tcaattggta cgtggacggc      600
gtggaagtgc acaacgccaa gaccaagccc agagaggaac agtacaactc cacctaccgg      660
gtggtgtccg tgctgaccgt gctgcaccag gattggctga acggcaaaga gtacaagtgc      720
aaggtgtcca caaggcccct gcctgcctcc atcgaaaaga ccatctccaa ggccaagggc      780
cagccccggg aaccccaggt gtacacactg ccccctagcc gggaagagat gacaaagaac      840
caggtgtccc tgacctgtct cgtgaaggga ttctaccct ccgatatcgc cgtggaatgg      900
gagtccaacg gccagcctga gaacaactac aagaccaccc ccctgtgct ggactccgac      960
ggctcattct tcctgtactc caagctgaca gtggacaagt cccggtggca gcagggcaac     1020
gtgttctcct gctccgtgat gcacgaggcc ctgcacaacc actacaccca gaagtccctg     1080
tccctgagcc ccggc                                                      1095
```

<210> SEQ ID NO 19
<211> LENGTH: 343
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 19

```
Ala Val Leu Pro Gln Glu Glu Glu Gly Ser Gly Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110
```

```
Gly Gly Cys Gln Gly Asn Gly Asn Lys Phe Tyr Ser Glu Lys Glu Cys
        115                 120                 125

Arg Glu Tyr Cys Gly Val Ser Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Ala Ser Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320

Ser Cys Ser Val Met His Glu Ala Leu His Asn His Tyr Thr Gln Lys
                325                 330                 335

Ser Leu Ser Leu Ser Pro Gly
            340

<210> SEQ ID NO 20
<211> LENGTH: 1029
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 20
gctgtgctgc tcaggaaga ggaaggctct ggcggaggcc agctcgtgac cgaagtgacc        60
aagaaagagg actcctgcca gctgggctac tctgccggcc cttgtatggg catgaccctc      120
cggtacttct acaacggcac ctccatggcc tgcgagacat tccagtacgg cggctgcatg      180
ggcaacggca caactttgt gacagagaaa gagtgcctgc agacctgcag aaccgtggcc       240
gcctgtaacc tgcctatcgt gcggggaccc tgtcgggcct tatccagct gtgggccttc       300 gacgccgtga agggcaaatg cgtgctgttc ccctatggcg gctgccaggg aaatggaaac      360
aagttctact ccgagaaaga atgccgcgag tactgtggcg tgtcctctgt gttcctgttc      420 ccccccaaagc ccaaggacac cctgatgatc tcccggaccc ctgaagtgac ctgcgtggtg     480
gtggatgtgt cccacgagga tcccgaagtg aagttcaatt ggtacgtgga cggcgtggaa      540
gtgcacaacg ccaagaccaa gcccagagag gaacagtaca actccaccta ccgggtggtg     600
tccgtgctga ccgtgctgca ccaggattgg ctgaacggca agagtacaa gtgcaaggtg       660
```

-continued

```
tccaacaagg ccctgcctgc ctccatcgaa aagaccatct ccaaggccaa gggccagccc    720
cgggaacccc aggtgtacac actgccccct agccgggaag agatgacaaa gaaccaggtg    780
tccctgacct gtctcgtgaa gggattctac ccctccgata tcgccgtgga atgggagtcc    840
aacggccagc tgagaacaa ctacaagacc ccccccctg tgctggactc cgacggctca     900
ttcttcctgt actccaagct gacagtggac aagtcccggt ggcagcaggg caacgtgttc    960
tcctgctccg tgatgcacga ggccctgcac aaccactaca cccagaagtc cctgtccctg   1020
agccccggc                                                           1029
```

<210> SEQ ID NO 21
<211> LENGTH: 375
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 21

```
Ala Val Leu Pro Gln Glu Glu Gly Ser Gly Gly Gly Gln Leu Val
1               5                   10                  15

Thr Glu Val Thr Ser Ser Glu Asp Ser Cys Gln Leu Gly Tyr Ser Ala
                20                  25                  30

Gly Pro Cys Met Gly Met Thr Ser Arg Tyr Phe Tyr Asn Gly Thr Ser
            35                  40                  45

Met Ala Cys Glu Thr Phe Gln Tyr Gly Gly Cys Met Gly Asn Gly Asn
50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Arg
    130                 135                 140

Glu Pro Lys Ser Ser Asp Lys Thr His Thr Cys Pro Pro Cys Pro Ala
145                 150                 155                 160

Pro Glu Leu Leu Gly Gly Ser Ser Val Phe Leu Phe Pro Pro Lys Pro
                165                 170                 175

Lys Asp Thr Leu Met Ile Ser Arg Thr Pro Glu Val Thr Cys Val Val
            180                 185                 190

Val Asp Val Ser His Glu Asp Pro Glu Val Lys Phe Asn Trp Tyr Val
        195                 200                 205

Asp Gly Val Glu Val His Asn Ala Lys Thr Lys Pro Arg Glu Glu Gln
    210                 215                 220

Tyr Asn Ser Thr Tyr Arg Val Val Ser Val Leu Thr Val Leu His Gln
225                 230                 235                 240

Asp Trp Leu Asn Gly Lys Glu Tyr Lys Cys Lys Val Ser Asn Lys Ala
                245                 250                 255

Leu Pro Ala Ser Ile Glu Lys Thr Ile Ser Lys Ala Lys Gly Gln Pro
            260                 265                 270

Arg Glu Pro Gln Val Tyr Thr Leu Pro Pro Ser Arg Glu Glu Met Thr
```

```
                275                 280                 285
Lys Asn Gln Val Ser Leu Thr Cys Leu Val Lys Gly Phe Tyr Pro Ser
            290                 295                 300

Asp Ile Ala Val Glu Trp Glu Ser Asn Gly Gln Pro Glu Asn Asn Tyr
305                 310                 315                 320

Lys Thr Thr Pro Pro Val Leu Asp Ser Asp Gly Ser Phe Phe Leu Tyr
                325                 330                 335

Ser Lys Leu Thr Val Asp Lys Ser Arg Trp Gln Gln Gly Asn Val Phe
            340                 345                 350

Ser Cys Ser Val Met His Glu Ala Leu His Asn His Tyr Thr Gln Lys
                355                 360                 365

Ser Leu Ser Leu Ser Pro Gly
            370                 375

<210> SEQ ID NO 22
<211> LENGTH: 1125
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 22
gctgtgctgc tcaggaaga ggaaggctct ggcggaggcc agctcgtgac cgaagtgacc      60
tcctccgagg actcctgcca gctgggctac tctgccggcc cttgtatggg catgacctcc    120
cggtacttct acaacggcac ctccatggcc tgcgagacat ccagtacgg cggctgcatg     180 ggcaacggca caactttgt gacagagaaa gagtgcctgc agacctgcag aaccgtggcc    240
gcctgtaacc tgcctatcgt gcggggaccc tgtcgggcct tatccagct gtgggccttc     300 gacgccgtga agggcaaatg cgtgctgttc ccctatggcg gctgccaggg aaatggaaac    360
aagttctact ccgagaaaga atgccgcgag tactgtggcg tgccaggcga cggggatgag    420
gaactgctgc gggagcccaa atcttccgac aagacccata cctgtccacc ttgccctgcc    480
cccgagctgc tgggaggatc ctctgtgttc ctgttccccc caaagcccaa ggacaccctg    540
atgatctccc ggacccctga agtgacctgc gtggtggtgg atgtgtccca cgaggatccc    600
gaagtgaagt tcaattggta cgtggacggc gtggaagtgc acaacgccaa gaccaagccc    660
agagaggaac agtacaactc cacctaccgg gtggtgtccg tgctgaccgt gctgcaccag    720
gattggctga acggcaaaga gtacaagtgc aaggtgtcca acaaggccct gcctgcctcc    780
atcgaaaaga ccatctccaa ggccaagggc cagccccggg aaccccaggt gtacacactg    840
ccccctagcc gggaagagat gacaaagaac caggtgtccc tgacctgtct cgtgaaggga    900
ttctacccct ccgatatcgc cgtggaatgg gagtccaacg ccagcctga acaactac      960 aagaccaccc cccctgtgct ggactccgac ggctcattct cctgtactc caagctgaca   1020 gtggacaagt cccggtggca gcagggcaac gtgttctcct gctccgtgat gcacgaggcc   1080
ctgcacaacc actacaccca gaagtccctg tccctgagcc ccggc                  1125

<210> SEQ ID NO 23
<211> LENGTH: 320
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 23

| | | | | | | | | | | | | | | |
|---|---|---|---|---|---|---|---|---|---|---|---|---|---|---|
|Ala|Val|Leu|Pro|Gln|Glu|Glu|Gly|Ser|Gly|Gly|Gly|Gln|Leu|Val|
|1| | | |5| | | |10| | | | |15| |
|Thr|Glu|Val|Thr|Lys|Lys|Thr|Val|Ala|Ala|Cys|Asn|Leu|Pro|Ile|Val|
| | | |20| | | | |25| | | | |30| |
|Arg|Gly|Pro|Cys|Arg|Ala|Phe|Ile|Gln|Leu|Trp|Ala|Phe|Asp|Ala|Val|
| | | |35| | | | |40| | | | |45| |
|Lys|Gly|Lys|Cys|Val|Leu|Phe|Pro|Tyr|Gly|Cys|Gln|Gly|Asn|Gly|
| | |50| | | | |55| | | | |60| | |
|Asn|Lys|Phe|Tyr|Ser|Glu|Lys|Glu|Cys|Arg|Glu|Tyr|Cys|Gly|Val|Pro|
|65| | | | |70| | | | |75| | | | |80|
|Gly|Asp|Gly|Asp|Glu|Glu|Leu|Leu|Arg|Glu|Pro|Lys|Ser|Ser|Asp|Lys|
| | | | |85| | | | |90| | | | |95| |
|Thr|His|Thr|Cys|Pro|Pro|Cys|Pro|Ala|Pro|Glu|Leu|Leu|Gly|Gly|Ser|
| | | |100| | | | |105| | | | |110| | |
|Ser|Val|Phe|Leu|Phe|Pro|Pro|Lys|Pro|Lys|Asp|Thr|Leu|Met|Ile|Ser|
| | |115| | | | |120| | | | |125| | | |
|Arg|Thr|Pro|Glu|Val|Thr|Cys|Val|Val|Val|Asp|Val|Ser|His|Glu|Asp|
| |130| | | | |135| | | | |140| | | | |
|Pro|Glu|Val|Lys|Phe|Asn|Trp|Tyr|Val|Asp|Gly|Val|Glu|Val|His|Asn|
|145| | | | |150| | | | |155| | | | |160|
|Ala|Lys|Thr|Lys|Pro|Arg|Glu|Glu|Gln|Tyr|Asn|Ser|Thr|Tyr|Arg|Val|
| | | | |165| | | | |170| | | | |175| |
|Val|Ser|Val|Leu|Thr|Val|Leu|His|Gln|Asp|Trp|Leu|Asn|Gly|Lys|Glu|
| | | |180| | | | |185| | | | |190| | |
|Tyr|Lys|Cys|Lys|Val|Ser|Asn|Lys|Ala|Leu|Pro|Ala|Ser|Ile|Glu|Lys|
| | |195| | | | |200| | | | |205| | | |
|Thr|Ile|Ser|Lys|Ala|Lys|Gly|Gln|Pro|Arg|Glu|Pro|Gln|Val|Tyr|Thr|
| |210| | | | |215| | | | |220| | | | |
|Leu|Pro|Pro|Ser|Arg|Glu|Glu|Met|Thr|Lys|Asn|Gln|Val|Ser|Leu|Thr|
|225| | | | |230| | | | |235| | | | |240|
|Cys|Leu|Val|Lys|Gly|Phe|Tyr|Pro|Ser|Asp|Ile|Ala|Val|Glu|Trp|Glu|
| | | | |245| | | | |250| | | | |255| |
|Ser|Asn|Gly|Gln|Pro|Glu|Asn|Asn|Tyr|Lys|Thr|Thr|Pro|Pro|Val|Leu|
| | | |260| | | | |265| | | | |270| | |
|Asp|Ser|Asp|Gly|Ser|Phe|Phe|Leu|Tyr|Ser|Lys|Leu|Thr|Val|Asp|Lys|
| | |275| | | | |280| | | | |285| | | |
|Ser|Arg|Trp|Gln|Gln|Gly|Asn|Val|Phe|Ser|Cys|Ser|Val|Met|His|Glu|
| |290| | | | |295| | | | |300| | | | |
|Ala|Leu|His|Asn|His|Tyr|Thr|Gln|Lys|Ser|Leu|Ser|Leu|Ser|Pro|Gly|
|305| | | | |310| | | | |315| | | | |320|

<210> SEQ ID NO 24
<211> LENGTH: 960
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 24

```
gctgtgctgc ctcaggaaga ggaaggctct ggcggaggcc agctcgtgac cgaagtgacc      60
aagaaaaccg tggccgcctg taacctgcct atcgtgcggg gaccctgtcg ggcctttatc     120
```

```
cagctgtggg ccttcgacgc cgtgaagggc aaatgcgtgc tgttcccta tggcggctgc      180
cagggaaatg gaaacaagtt ctactccgag aaagaatgcc gcgagtactg tggcgtgcca      240
ggcgacgggg atgaggaact gctgcgggag cccaaatctt ccgacaagac ccatacctgt      300
ccaccttgcc ctgcccccga gctgctggga ggatcctctg tgttcctgtt cccccaaag      360
cccaaggaca ccctgatgat ctcccggacc cctgaagtga cctgcgtggt ggtggatgtg      420
tcccacgagg atcccgaagt gaagttcaat tggtacgtgg acggcgtgga agtgcacaac      480
gccaagacca agcccagaga ggaacagtac aactccacct accgggtggt gtccgtgctg      540
accgtgctgc accaggattg gctgaacggc aaagagtaca agtgcaaggt gtccaacaag      600
gccctgcctg cctccatcga aaagaccatc tccaaggcca agggccagcc ccgggaaccc      660
caggtgtaca cactgccccc tagccgggaa gagatgacaa agaaccaggt gtccctgacc      720
tgtctcgtga agggattcta ccctccgat atcgccgtgg aatgggagtc caacggccag      780
cctgagaaca actacaagac cacccccct gtgctggact ccgacggctc attcttcctg      840
tactccaagc tgacagtgga caagtcccgg tggcagcagg gcaacgtgtt ctcctgctcc      900
gtgatgcacg aggccctgca caaccactac acccagaagt ccctgtccct gagccccggc      960

<210> SEQ ID NO 25
<211> LENGTH: 308
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Val Leu Pro Gln Glu Glu Gly Ser Gly Gly Gly Gln Leu Val
1               5                   10                  15

Thr Glu Val Thr Lys Lys Glu Asp Ser Cys Gln Leu Gly Tyr Ser Ala
                20                  25                  30

Gly Pro Cys Met Gly Met Thr Ser Arg Tyr Phe Tyr Asn Gly Thr Ser
            35                  40                  45

Met Ala Cys Glu Thr Phe Gln Tyr Gly Gly Cys Met Gly Asn Gly Asn
        50                  55                  60

Asn Phe Val Thr Glu Lys Glu Cys Leu Gln Thr Cys Arg Glu Pro Lys
65                  70                  75                  80

Ser Ser Asp Lys Thr His Thr Cys Pro Pro Cys Pro Ala Pro Glu Leu
                85                  90                  95

Leu Gly Gly Ser Ser Val Phe Leu Phe Pro Pro Lys Pro Lys Asp Thr
            100                 105                 110

Leu Met Ile Ser Arg Thr Pro Glu Val Thr Cys Val Val Val Asp Val
        115                 120                 125

Ser His Glu Asp Pro Glu Val Lys Phe Asn Trp Tyr Val Asp Gly Val
    130                 135                 140

Glu Val His Asn Ala Lys Thr Lys Pro Arg Glu Glu Gln Tyr Asn Ser
145                 150                 155                 160

Thr Tyr Arg Val Val Ser Val Leu Thr Val Leu His Gln Asp Trp Leu
                165                 170                 175

Asn Gly Lys Glu Tyr Lys Cys Lys Val Ser Asn Lys Ala Leu Pro Ala
            180                 185                 190

Ser Ile Glu Lys Thr Ile Ser Lys Ala Lys Gly Gln Pro Arg Glu Pro
        195                 200                 205
```

Gln Val Tyr Thr Leu Pro Pro Ser Arg Glu Glu Met Thr Lys Asn Gln
210                 215                 220

Val Ser Leu Thr Cys Leu Val Lys Gly Phe Tyr Pro Ser Asp Ile Ala
225                 230                 235                 240

Val Glu Trp Glu Ser Asn Gly Gln Pro Glu Asn Asn Tyr Lys Thr Thr
            245                 250                 255

Pro Pro Val Leu Asp Ser Asp Gly Ser Phe Phe Leu Tyr Ser Lys Leu
        260                 265                 270

Thr Val Asp Lys Ser Arg Trp Gln Gln Gly Asn Val Phe Ser Cys Ser
            275                 280                 285

Val Met His Glu Ala Leu His Asn His Tyr Thr Gln Lys Ser Leu Ser
290                 295                 300

Leu Ser Pro Gly
305

<210> SEQ ID NO 26
<211> LENGTH: 924
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 26
gctgtgctgc ctcaggaaga ggaaggctct ggcggaggcc agctcgtgac cgaagtgacc      60
aagaaagagg actcctgcca gctgggctac tctgccggcc cttgtatggg catgaccctc     120
cggtacttct acaacggcac ctccatggcc tgcgagacat ccagtacgg cggctgcatg     180 ggcaacggca caactttgt gacagagaaa gagtgcctgc agacctgcag agagcccaaa     240
tcttccgaca gacccatac ctgtccacct tgccctgccc ccgagctgct gggaggatcc     300
tctgtgttcc tgttcccccc aaagcccaag gacaccctga tgatctcccg gacccctgaa     360
gtgacctgcg tggtggtgga tgtgtcccac gaggatcccg aagtgaagtt caattggtac     420
gtggacggcg tggaagtgca caacgccaag accaagccca gagaggaaca gtacaactcc     480
acctaccggg tggtgtccgt gctgaccgtg ctgcaccagg attggctgaa cggcaaagag     540
tacaagtgca aggtgtccaa caaggccctg cctgcctcca tcgaaaagac catctccaag     600
gccaagggcc agccccggga acccccaggtg tacacactgc cccctagccg ggaagagatg     660
acaaagaacc aggtgtccct gacctgtctc gtgaagggat tctacccctc cgatatcgcc     720
gtggaatggg agtccaacgg ccagcctgag aacaactaca agaccacccc ccctgtgctg     780
gactccgacg gctcattctt cctgtactcc aagctgacag tggacaagtc ccggtggcag     840
cagggcaacg tgttctcctg ctccgtgatg cacgaggccc tgcacaacca ctacacccag     900
aagtccctgt ccctgagccc cggc                                            924

<210> SEQ ID NO 27
<211> LENGTH: 374
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ala Val Leu Pro Gln Glu Ser Glu Gly Ser Gly Thr Glu Pro Leu Ile
1               5                   10                  15

Thr Gly Thr Leu Lys Lys Glu Asp Ser Cys Gln Leu Asn Tyr Ser Glu
        20                  25                  30

Gly Pro Cys Leu Gly Met Gln Glu Arg Tyr Tyr Asn Gly Ala Ser
            35                  40                  45

Met Ala Cys Glu Thr Phe Gln Tyr Gly Gly Cys Leu Gly Asn Gly Asn
 50                  55                  60

Asn Phe Ile Ser Glu Lys Asp Cys Leu Gln Thr Cys Arg Thr Ile Ala
 65                  70                  75                  80

Ala Cys Asn Leu Pro Ile Val Gln Gly Pro Cys Arg Ala Phe Ile Lys
                85                  90                  95

Leu Trp Ala Phe Asp Ala Ala Gln Gly Lys Cys Ile Gln Phe His Tyr
            100                 105                 110

Gly Gly Cys Lys Gly Asn Gly Asn Lys Phe Tyr Ser Glu Lys Glu Cys
            115                 120                 125

Lys Glu Tyr Cys Gly Val Pro Gly Asp Gly Tyr Glu Glu Leu Ile Arg
130                 135                 140

Ser Lys Ile Val Pro Arg Asp Cys Gly Cys Lys Pro Cys Ile Cys Thr
145                 150                 155                 160

Val Pro Glu Val Ser Ser Val Phe Ile Phe Pro Pro Lys Pro Lys Asp
                165                 170                 175

Val Leu Thr Ile Thr Leu Thr Pro Lys Val Thr Cys Val Val Val Asp
            180                 185                 190

Ile Ser Lys Asp Asp Pro Glu Val Gln Phe Ser Trp Phe Val Asp Asp
        195                 200                 205

Val Glu Val His Thr Ala Gln Thr Gln Pro Arg Glu Glu Gln Phe Asn
    210                 215                 220

Ser Thr Phe Arg Ser Val Ser Glu Leu Pro Ile Met His Gln Asp Trp
225                 230                 235                 240

Leu Asn Gly Lys Glu Phe Lys Cys Arg Val Asn Ser Ala Ala Phe Pro
                245                 250                 255

Ala Pro Ile Glu Lys Thr Ile Ser Lys Thr Lys Gly Arg Pro Lys Ala
            260                 265                 270

Pro Gln Val Tyr Thr Ile Pro Pro Lys Glu Gln Met Ala Lys Asp
        275                 280                 285

Lys Val Ser Leu Thr Cys Met Ile Thr Asp Phe Phe Pro Glu Asp Ile
290                 295                 300

Thr Val Glu Trp Gln Trp Asn Gly Gln Pro Ala Glu Asn Tyr Lys Asn
305                 310                 315                 320

Thr Gln Pro Ile Met Asp Thr Asp Gly Ser Tyr Phe Val Tyr Ser Lys
            325                 330                 335

Leu Asn Val Gln Lys Ser Asn Trp Glu Ala Gly Asn Thr Phe Thr Cys
            340                 345                 350

Ser Val Leu His Glu Gly Leu His Asn His Thr Glu Lys Ser Leu
            355                 360                 365

Ser His Ser Pro Gly Lys
    370

<210> SEQ ID NO 28
<211> LENGTH: 1122
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic polynucleotide"

<400> SEQUENCE: 28

```
gcagtgctgc cccaagagag tgagggggtca gggactgagc cactaataac tgggaccctc        60
aagaaagaag actcctgcca gctcaattac tcagaaggcc cctgcctagg gatgcaagag       120
aggtattact acaacggcgc ttccatggcc tgcgagacct ttcaatatgg gggttgccta       180
ggcaacggca caacttcat ctctgagaag gactgtctgc agacatgtcg gaccatagcg       240
gcctgcaatc tccccatagt ccaaggcccc tgccgagcct tcataaagct ctgggcattt       300
gatgcagcac aagggaagtg catccaattc cactacgggg gctgcaaagg caacggcaac       360
aaattctact ctgagaagga atgcaaagag tactgtggag tccctggtga tgggtacgag       420
gaactaatac gcagtaaaat cgtgcctcgg gactgcggct gcaagccctg catctgcacc       480
gtgcccgagg tgtcctccgt gttcatcttc ccacccaagc ccaaggacgt gctgaccatc       540
accctgaccc ccaaagtgac ctgcgtggtg gtggacatct ccaaggacga ccccgaggtg       600
cagttcagtt ggttcgtgga cgacgtggaa gtgcacaccg cccagaccca gcccagagag       660
gaacagttca actccaccct tcagatccgtg tccgagctgc ccatcatgca ccaggactgg       720
ctgaacggca aagagttcaa gtgcagagtg aactccgccg ccttcccagc ccccatcgaa       780
aagaccatct ccaagaccaa gggcagaccc aaggcccccc aggtgtacac catcccccca       840
cccaagaac agatggccaa ggacaaggtg tccctgacct gcatgatcac cgatttcttc       900
ccagaggaca tcaccgtgga atggcagtgg aacggccagc ccgccgagaa ctacaagaac       960
acccagccca tcatggacac cgacggctcc tacttcgtgt actccaagct gaacgtgcag      1020
aagtccaact gggaggccgg caacaccttc acctgtagcg tgctgcacga gggcctgcac      1080
aaccaccaca ccgagaagtc cctgtcccac tcccccggca ag                         1122
```

<210> SEQ ID NO 29
<211> LENGTH: 391
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 29

```
Glu Pro Lys Ser Ser Asp Lys Thr His Thr Cys Pro Pro Cys Pro Ala
1               5                  10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140
```

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
            165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Ser Gly Gly Gly
225                 230                 235                 240

Gly Ser Gly Gly Gly Ser Ala Val Leu Pro Gln Glu Glu Glu Gly
            245                 250                 255

Ser Gly Gly Gly Gln Leu Val Thr Glu Val Thr Lys Lys Glu Asp Ser
            260                 265                 270

Cys Gln Leu Gly Tyr Ser Ala Gly Pro Cys Met Gly Met Thr Ser Arg
        275                 280                 285

Tyr Phe Tyr Asn Gly Thr Ser Met Ala Cys Glu Thr Phe Gln Tyr Gly
    290                 295                 300

Gly Cys Met Gly Asn Gly Asn Asn Phe Val Thr Glu Lys Glu Cys Leu
305                 310                 315                 320

Gln Thr Cys Arg Thr Val Ala Ala Cys Asn Leu Pro Ile Val Arg Gly
            325                 330                 335

Pro Cys Arg Ala Phe Ile Gln Leu Trp Ala Phe Asp Ala Val Lys Gly
            340                 345                 350

Lys Cys Val Leu Phe Pro Tyr Gly Gly Cys Gln Gly Asn Gly Asn Lys
        355                 360                 365

Phe Tyr Ser Glu Lys Glu Cys Arg Glu Tyr Cys Gly Val Pro Gly Asp
    370                 375                 380

Gly Asp Glu Glu Leu Leu Arg
385                 390

<210> SEQ ID NO 30
<211> LENGTH: 1173
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 30
gagcccaaat cttccgacaa gacccatacc tgtccacctt gccctgcccc cgagctgctg      60
ggaggatcct ctgtgttcct gttccccca aagcccaagg acaccctgat gatctcccgg     120 accccctgaag tgacctgcgt ggtggtggat gtgtcccacg aggatcccga agtgaagttc     180
aattggtacg tggacggcgt ggaagtgcac aacgccaaga ccaagcccag agaggaacag     240
tacaactcca cctaccgggt ggtgtccgtg ctgaccgtgc tgcaccagga ttggctgaac     300
ggcaaagagt acaagtgcaa ggtgtccaac aaggccctgc ctgcctccat cgaaaagacc     360
atctccaagg ccaagggcca gccccgggaa ccccaggtgt acacactgcc cctagccgg     420 gaagagatga caaagaacca ggtgtccctg acctgtctcg tgaagggatt ctacccctcc     480
gatatcgccg tggaatggga gtccaacggc cagcctgaga caactacaa gaccaccccc     540

```
cctgtgctgg actccgacgg ctcattcttc ctgtactcca agctgacagt ggacaagtcc    600
cggtggcagc agggcaacgt gttctcctgc tccgtgatgc acgaggccct gcacaaccac    660
tacacccaga agtccctgtc cctgagcccc ggcaagggag gtggtggatc aggaggtgga    720
ggttccggtg gcggaggatc agctgtgctg cctcaggaag aggaaggctc tggcggaggc    780
cagctcgtga ccgaagtgac caagaaagag gactcctgcc agctgggcta ctctgccggc    840
ccttgtatgg gcatgacctc ccggtacttc tacaacggca cctccatggc ctgcgagaca    900
ttccagtacg gcggctgcat gggcaacggc aacaactttg tgacagagaa agagtgcctg    960
cagacctgca gaaccgtggc cgcctgtaac ctgcctatcg tgggggaccc tgtcgggcc   1020 tttatccagc tgtgggcctt cgacgccgtg aagggcaaat gcgtgctgtt ccccatggc   1080 ggctgccagg gaaatggaaa caagttctac tccgagaaag aatgccgcga gtactgtggc   1140
gtgccaggcg acggggatga ggaactgctg cgg                                1173
```

<210> SEQ ID NO 31
<211> LENGTH: 147
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Ala Val Leu Pro Gln Glu Glu Gly Ser Gly Gly Gln Leu Val
1               5                   10                  15

Thr Glu Val Thr Lys Lys Glu Asp Ser Cys Gln Leu Gly Tyr Ser Ala
            20                  25                  30

Gly Pro Cys Met Gly Met Thr Ser Arg Tyr Phe Tyr Asn Gly Thr Ser
        35                  40                  45

Met Ala Cys Glu Thr Phe Gln Tyr Gly Gly Cys Met Gly Asn Gly Asn
    50                  55                  60

Asn Phe Val Thr Glu Lys Glu Cys Leu Gln Thr Cys Arg Thr Val Ala
65                  70                  75                  80

Ala Cys Asn Leu Pro Ile Val Arg Gly Pro Cys Arg Ala Phe Ile Gln
                85                  90                  95

Leu Trp Ala Phe Asp Ala Val Lys Gly Lys Cys Val Leu Phe Pro Tyr
            100                 105                 110

Gly Gly Cys Gln Gly Asn Gly Asn Lys Phe Tyr Ser Glu Lys Glu Cys
        115                 120                 125

Arg Glu Tyr Cys Gly Val Pro Gly Asp Gly Asp Glu Glu Leu Leu Arg
    130                 135                 140

Phe Ser Asn
145

<210> SEQ ID NO 32
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Met Arg Ser Leu Gly Ala Leu Leu Leu Leu Ser Ala Cys Leu Ala
1               5                   10                  15

```
Val Ser Ala Gly Pro Val Pro Thr Pro Pro Asp Asn Ile Gln Val Gln
            20                  25                  30

Glu Asn Phe Asn Ile Ser Arg Ile Tyr Gly Lys Trp Tyr Asn Leu Ala
        35                  40                  45

Ile Gly Ser Thr Cys Pro Trp Leu Lys Lys Ile Met Asp Arg Met Thr
    50                  55                  60

Val Ser Thr Leu Val Leu Gly Glu Gly Ala Thr Glu Ala Glu Ile Ser
65                  70                  75                  80

Met Thr Ser Thr Arg Trp Arg Lys Gly Val Cys Glu Glu Thr Ser Gly
                85                  90                  95

Ala Tyr Glu Lys Thr Asp Thr Asp Gly Lys Phe Leu Tyr His Lys Ser
            100                 105                 110

Lys Trp Asn Ile Thr Met Glu Ser Tyr Val Val His Thr Asn Tyr Asp
        115                 120                 125

Glu Tyr Ala Ile Phe Leu Thr Lys Lys Phe Ser Arg His His Gly Pro
    130                 135                 140

Thr Ile Thr Ala Lys Leu Tyr Gly Arg Ala Pro Gln Leu Arg Glu Thr
145                 150                 155                 160

Leu Leu Gln Asp Phe Arg Val Val Ala Gln Gly Val Gly Ile Pro Glu
                165                 170                 175

Asp Ser Ile Phe Thr Met Ala Asp Arg Gly Glu Cys Val Pro Gly Glu
            180                 185                 190

Gln Glu Pro Glu Pro Ile Leu Ile Pro Arg Val Arg Arg Ala Val Leu
        195                 200                 205

Pro Gln Glu Glu Glu Gly Ser Gly Gly Gly Leu Val Thr Glu Val
210                 215                 220

Thr Lys Lys Glu Asp Ser Cys Gln Leu Gly Tyr Ser Ala Gly Pro Cys
225                 230                 235                 240

Met Gly Met Thr Ser Arg Tyr Phe Tyr Asn Gly Thr Ser Met Ala Cys
                245                 250                 255

Glu Thr Phe Gln Tyr Gly Gly Cys Met Gly Asn Gly Asn Asn Phe Val
            260                 265                 270

Thr Glu Lys Glu Cys Leu Gln Thr Cys Arg Thr Val Ala Ala Cys Asn
        275                 280                 285

Leu Pro Ile Val Arg Gly Pro Cys Arg Ala Phe Ile Gln Leu Trp Ala
    290                 295                 300

Phe Asp Ala Val Lys Gly Lys Cys Val Leu Phe Pro Tyr Gly Gly Cys
305                 310                 315                 320

Gln Gly Asn Gly Asn Lys Phe Tyr Ser Glu Lys Glu Cys Arg Glu Tyr
                325                 330                 335

Cys Gly Val Pro Gly Asp Gly Asp Glu Glu Leu Leu Arg Phe Ser Asn
            340                 345                 350

<210> SEQ ID NO 33
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Ser Gly Gly Gly Gly Ser
1               5
```

```
<210> SEQ ID NO 34
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ser Gly Gly Gly Gly Ser Gly Gly Gly Gly Ser
1               5                   10

<210> SEQ ID NO 35
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 35

Ser Gly Gly Gly Gly Ser Gly Gly Gly Gly Ser Gly Gly Gly Gly Ser
1               5                   10                  15

<210> SEQ ID NO 36
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 36

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 37
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 37

Ser Gly Gly Gly Gly Ser Gly Gly Gly Ser Gly Gly Gly Gly Ser
1               5                   10                  15

Gly Gly Gly Gly Ser Gly Gly Gly Gly Ser
            20                  25

<210> SEQ ID NO 38
<211> LENGTH: 31
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ser Gly Gly Gly Gly Ser Gly Gly Gly Gly Ser Gly Gly Gly Gly Ser
1               5                   10                  15
```

Gly Gly Gly Gly Ser Gly Gly Gly Ser Gly Gly Gly Gly Ser
            20                  25                  30

<210> SEQ ID NO 39
<211> LENGTH: 36
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser
        35

<210> SEQ ID NO 40
<211> LENGTH: 41
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser
        35                  40

<210> SEQ ID NO 41
<211> LENGTH: 46
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser Gly Gly Gly Gly Ser Gly
            20                  25                  30

Gly Gly Gly Ser Gly Gly Gly Gly Ser Gly Gly Gly Gly Ser
        35                  40                  45

<210> SEQ ID NO 42
<211> LENGTH: 51
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

```
Ser Gly Gly Gly Gly Ser Gly Gly Gly Ser Gly Gly Gly Ser
1               5                  10                 15

Gly Gly Gly Gly Ser Gly Gly Gly Ser Gly Gly Gly Ser Gly
            20                  25                  30

Gly Gly Gly Ser Gly Gly Gly Ser Gly Gly Gly Ser Gly Gly
        35                  40                  45

Gly Gly Ser
    50
```

<210> SEQ ID NO 43
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 43

```
Gly Ser Gly Gly Gly Ser Gly Gly Gly Ser Gly Gly Gly Gly Ser
1               5                  10                 15
```

<210> SEQ ID NO 44
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 44

```
Met Gly Trp Ser Cys Ile Ile Leu Phe Leu Val Ala Thr Ala Thr Gly
1               5                  10                 15

Val His Ser
```

<210> SEQ ID NO 45
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 45

```
Pro Gly Asp Gly Asp Glu Glu Leu Leu Arg Glu Pro Lys Ser Ser Asp
1               5                  10                 15

Lys Thr His
```

<210> SEQ ID NO 46
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 46

```
Pro Gly Asp Gly Asp Glu Glu Leu Leu Gly Ser Gly Gly Gly Gly Asp
1               5                  10                 15

Lys Thr His
```

```
<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Gly Gly Gly Gly Ser Gly Gly Gly Gly Ser
1               5                   10

<210> SEQ ID NO 48
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 48

Gly Gly Gly Gly Ser Gly Gly Gly Gly Ser Gly Gly Gly Gly Ser
1               5                   10                  15
```